United States Patent
Leung et al.

(10) Patent No.: US 11,234,761 B2
(45) Date of Patent: Feb. 1, 2022

(54) ELECTROSURGICAL DEVICE FOR CREATING A CHANNEL THROUGH A REGION OF TISSUE AND METHODS OF USE THEREOF

(71) Applicant: Baylis Medical Company Inc., Montreal (CA)

(72) Inventors: Linus Hoi Che Leung, Toronto (CA); Mahban Samiee-Zafarghandy, Richmond Hill (CA); Rund Abou-Marie, Mississauga (CA); Taras Juzkiw, Mississauga (CA); Gareth Davies, Toronto (CA); Maria Luk, Kleinburg (CA); Kelly Albert, Brampton (CA)

(73) Assignee: Baylis Medical Company Inc., Mississauga (CA)

( * ) Notice: Subject to any disclaimer, the term of this patent is extended or adjusted under 35 U.S.C. 154(b) by 638 days.

(21) Appl. No.: 15/359,881

(22) Filed: Nov. 23, 2016

(65) Prior Publication Data
US 2017/0071667 A1 Mar. 16, 2017

Related U.S. Application Data

(63) Continuation-in-part of application No. 12/926,292, filed on Nov. 8, 2010, now Pat. No. 9,510,900, which
(Continued)

(51) Int. Cl.
*A61B 18/14* (2006.01)
*A61B 90/00* (2016.01)
(Continued)

(52) U.S. Cl.
CPC .......... *A61B 18/1492* (2013.01); *A61B 90/39* (2016.02); *A61B 18/1206* (2013.01); *A61B 2017/00867* (2013.01); *A61B 2018/0041* (2013.01); *A61B 2018/00083* (2013.01); *A61B 2018/00101* (2013.01); *A61B 2018/00136* (2013.01); *A61B 2018/00601* (2013.01); *A61B 2018/1213* (2013.01); *A61B 2090/3966* (2016.02); *C08L 2201/12* (2013.01)

(58) Field of Classification Search
CPC ............ A61B 18/1492; A61B 18/1206; A61B 2018/00083; A61B 2018/00101
See application file for complete search history.

(56) References Cited

U.S. PATENT DOCUMENTS 5,318,525 A * 6/1994 West .................. A61B 18/1492
600/585
5,509,411 A * 4/1996 Littmann ............. A61B 5/0422
600/381
(Continued)

*Primary Examiner* — Michael F Peffley
*Assistant Examiner* — Bo Ouyang
(74) *Attorney, Agent, or Firm* — Glenn Arnold; Vincent Man; Samuel Tekie

(57) ABSTRACT

A method and apparatus are disclosed for an RF guidewire for applying RF energy to create a channel through a region of tissue within a patient's body. The RF guidewire is configured to have a hydrophilic coating disposed thereon to reduce friction to facilitate traversal through vasculature while maintaining its mechanical, electrical and thermal properties.

18 Claims, 15 Drawing Sheets

Related U.S. Application Data is a continuation-in-part of application No. 11/627,406, filed on Jan. 26, 2007, now Pat. No. 8,092,450.

(60) Provisional application No. 60/743,181, filed on Jan. 27, 2006, provisional application No. 60/827,458, filed on Sep. 29, 2006.

(51) Int. Cl.
*A61B 18/00* (2006.01)
*A61B 18/12* (2006.01)
*A61B 17/00* (2006.01)

(56) References Cited

U.S. PATENT DOCUMENTS

| | | | | |
|---|---|---|---|---|
| 6,030,380 | A * | 2/2000 | Auth | A61B 18/1492 |
| | | | | 128/898 |
| 6,395,002 | B1 * | 5/2002 | Ellman | A61B 18/1485 |
| | | | | 606/45 |
| 2004/0181213 | A1 * | 9/2004 | Gondo | A61B 18/1402 |
| | | | | 606/33 |
| 2006/0041253 | A1 * | 2/2006 | Newton | A61B 18/1233 |
| | | | | 606/32 |
| 2006/0079884 | A1 * | 4/2006 | Manzo | A61B 34/30 |
| | | | | 606/41 |
| 2007/0167775 | A1 * | 7/2007 | Kochavi | A61B 5/6885 |
| | | | | 600/439 |

* cited by examiner

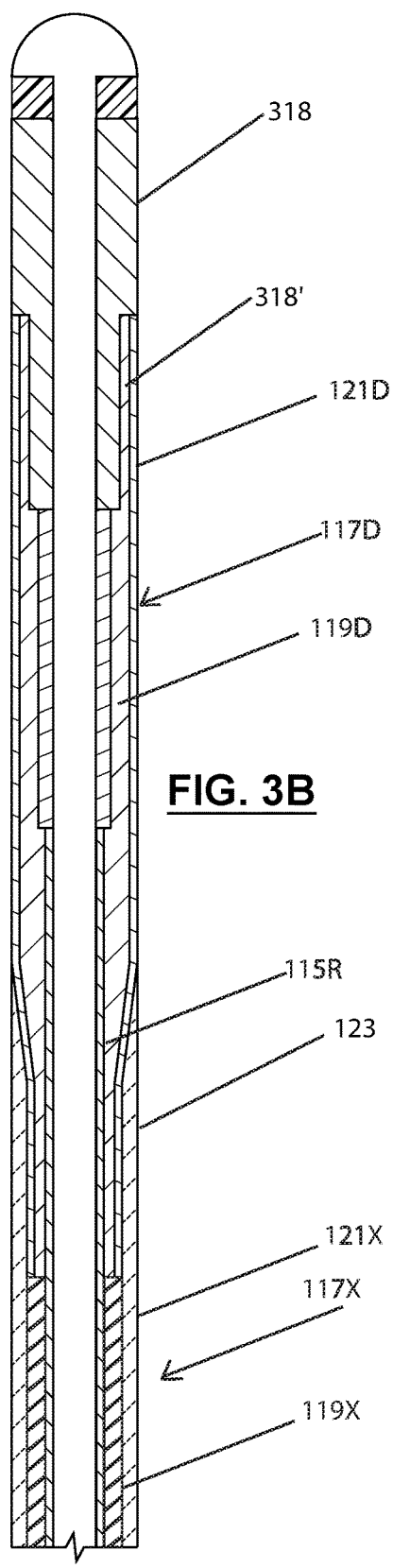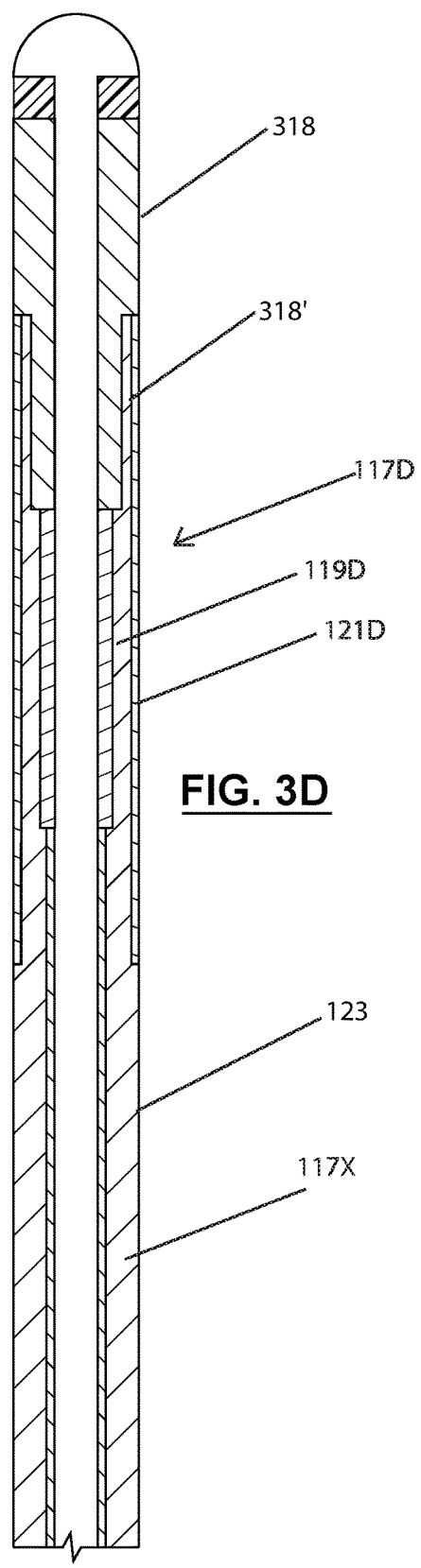

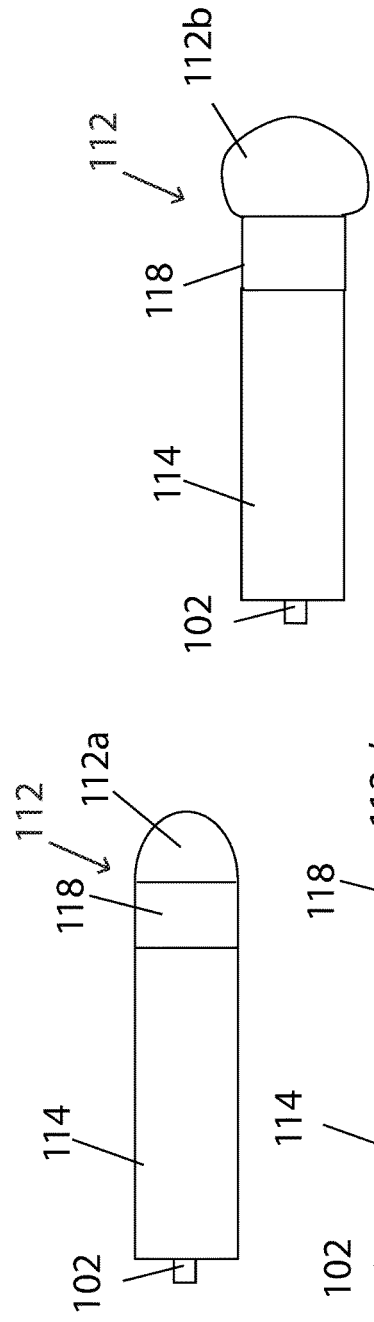
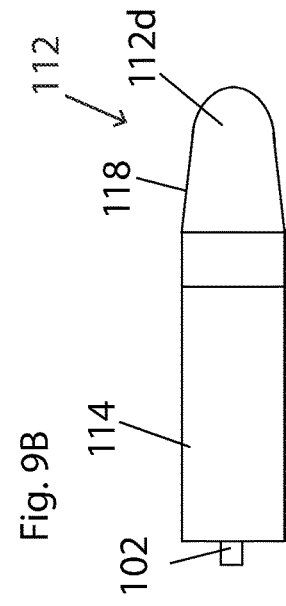
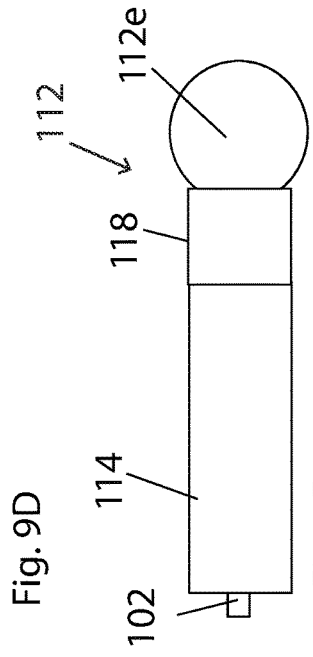
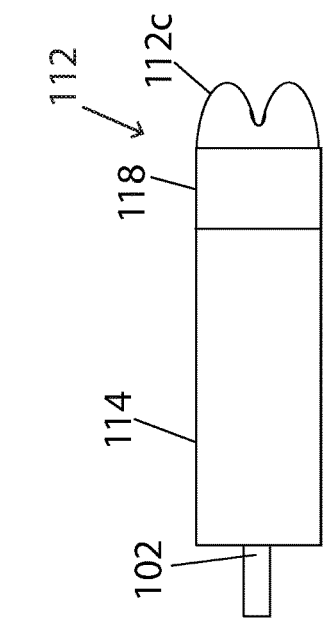

ELECTROSURGICAL DEVICE FOR CREATING A CHANNEL THROUGH A REGION OF TISSUE AND METHODS OF USE THEREOF

REFERENCES TO PARENT AND CO-PENDING APPLICATIONS

This is a continuation-in-part of U.S. patent application Ser. No. 12/926,292, filed on Nov. 8, 2010, which is a continuation-in-part of U.S. patent application Ser. No. 11/627,406, filed on Jan. 26, 2007, which is now U.S. Pat. No. 8,092,450, which claims the benefit of U.S. Provisional Patent Application Ser. No. 60/743,181, filed on Jan. 27, 2006 and U.S. Provisional Patent Application Ser. No. 60/827,458, filed on Sep. 29, 2006. The patent applications and provisional patent applications are all hereby incorporated by reference in their entirety.

TECHNICAL FIELD

The disclosure relates to an RF guidewire for applying RF energy to create a channel through a region of tissue within a patient's body. More specifically, the disclosure relates to an RF guidewire that is configured to have a hydrophilic coating disposed thereon to reduce friction to facilitate traversal through vasculature while maintaining its mechanical, electrical and thermal properties

BRIEF DESCRIPTION OF DRAWINGS

In order that the invention may be readily understood, embodiments of the invention are illustrated by way of examples in the accompanying drawings, in which:

FIGS. 3A-3D are an illustration of an electrosurgical device in accordance with still a further alternate embodiment of the present invention illustrating a novel architecture for an insulation layer;

FIGS. 9A-9E show the electrode in accordance with various embodiments of the present invention.

DETAILED DESCRIPTION

Figure 1A:
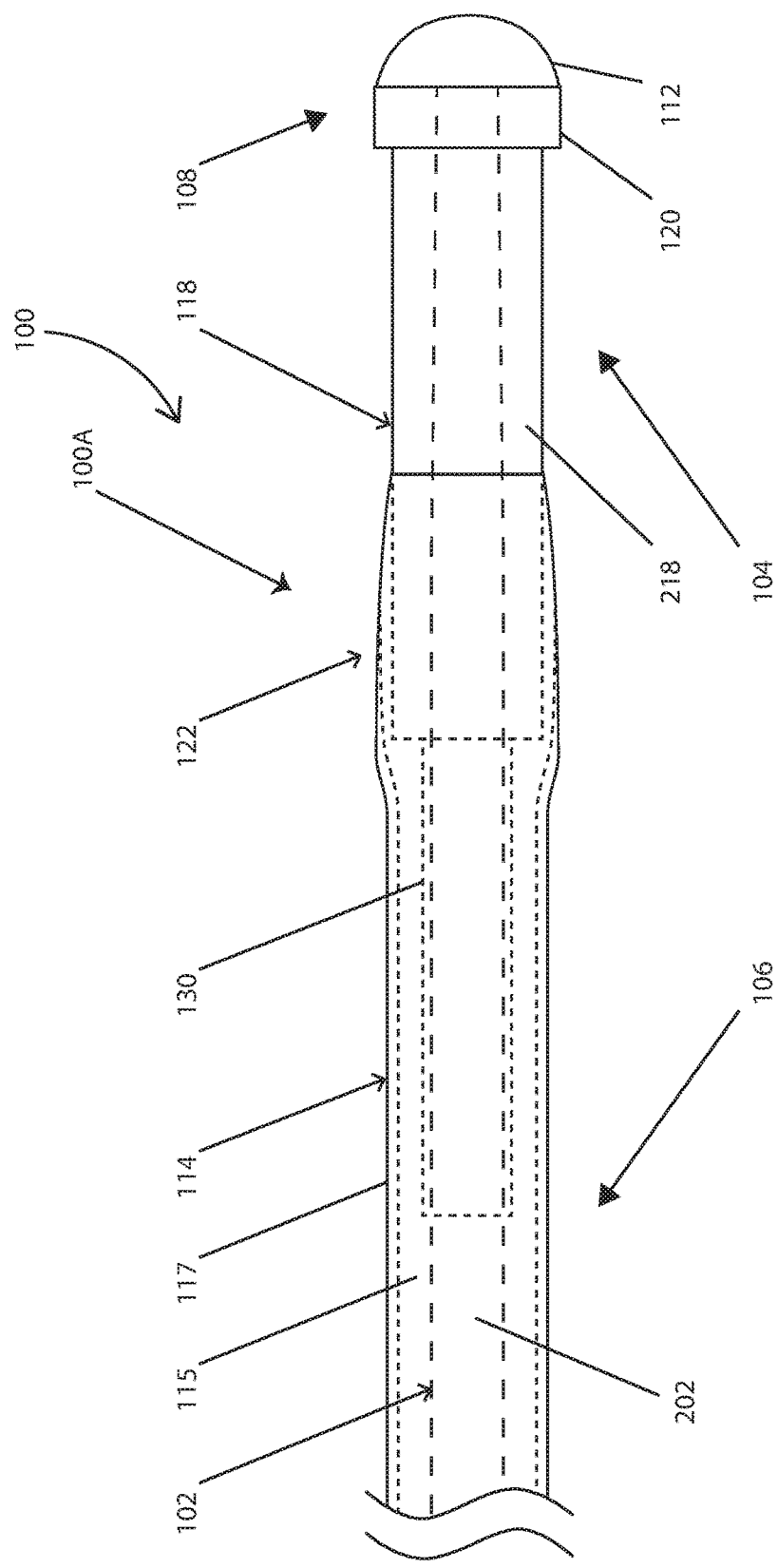
FIG. 1A-1B are an illustration of an electrosurgical device in accordance with an embodiment of the present invention.

Standard mechanical guidewires are used to provide general access into the body using minimally invasive techniques. In order to provide the functionality thereof, guidewires comprises mechanical properties that enable the guidewire to navigate through tortuous anatomy to reach the target site within the body. Some guidewires may comprise a hydrophilic coating to further ease and facilitate traversal through vasculature.

However, mechanical guidewires may have difficulty traversing through tough or calcified tissue. There is a need in the art to provide a guidewire that provides ease of traversal through vasculature and through a target tissue site within a patient's body.

As such, some embodiments of the present invention provide a guidewire that provides RF capabilities in addition to the mechanical properties provided by standard guidewires and additionally provides a hydrophilic coating to facilitate traversal through vasculature.

Hydrophilic coatings may significantly help reduce friction force on the surface of the device for example associated with insertion and/or advancement of a guidewire by forming dynamic hydrogen bonds with water. A hydrophilic coating possesses 'water loving' properties and therefore, is highly lubricious when working with body fluids and tissues. As such application of a hydrophilic coating to an RF guidewire may help reduce trauma or injury to the patient and may allow the RF guidewire to be inserted more smoothly and easily. Additionally, application of a hydrophilic coating on an RF guidewire may enhance the crossing ability of the RF guidewire through the occlusion.

Additionally, the hydrophilic coating may help enhance the tactile feedback to the physician as the RF guidewire is advanced inside the vasculature. The coating may significantly reduce the friction on the outer surface of the RF guidewire and in effect improve the signal-to-noise ratio on the tactile feedback. As such, more tactile feedback may be transferred to the physician since less noise (friction) may be present. In some examples, the chemistry of coatings involve a chemical bond between the coating and the substrate.

However, materials that are generally used for mechanical guidewires that are compatible with hydrophilic coatings may not provide adequate electrical and thermal insulation for an RF guidewire. Furthermore, materials that may provide adequate electrical and thermal resistivity or insulation for an RF guidewire may not be compatible with a hydrophilic coating. Some examples of conventional insulation layers used for mechanical guidewires may comprise a material that is naturally inert where the hydrophilic coating may not bond to the surface of the insulation layer and therefore may not be applied thereto.

As such there is a need in the prior art to provide an RF guidewire with a novel architecture for an insulation layer to enable a hydrophilic coating to be disposed thereon while at the same time maintaining the mechanical as well as electrical and heat resistive properties of the RF guidewire. Specifically, there is a need in the prior art for a an RF guidewire having a novel insulation layer architecture that provides the required insulation from the delivery of RF current and is additionally soft enough to have favorable mechanical properties to allow for tracking through various anatomies. In other words, an insulation layer is required that provides a unique combination of properties that include good flexibility and dielectric properties while accommodating a hydrophilic coating.

In one broad aspect, embodiments of the present invention provide an RF guidewire that overcomes the disadvantages associated with prior art devices for creating a channel through a region of tissue. In some embodiments, an RF guidewire is provided that additionally comprises a hydrophilic coating disposed along a portion thereof for ease of navigation through vasculature and/or tissue while providing: (i) sufficient electrical resistivity to minimize the risk of leakage current to maintain patient safety upon delivery of RF; (ii) sufficient mechanical flexibility to enable navigation through vascular anatomy to allow the RF guidewire to reach the intended target; and (iii) sufficient thermal insulation to protect the RF guidewire from heat produced through RF delivery at the distal tip. In some such embodiments, a hydrophilic RF guidewire is provided that overcomes the limitations associated with prior guidewires while maintaining its mechanical, electrical and thermal properties.

Current mechanical guidewires have several limitations which may include (i) the need to apply excessive force in order to traverse through tissue and/or (ii) inability to traverse through blockages or tough calcified tissue. Some such mechanical guidewires may provide a hydrophilic coating. However, mechanical guidewires that comprise a hydrophilic coating comprise polymers that are designed to provide sufficient mechanical flexibility and have the ability to have a hydrophilic coating disposed thereon, however, these polymers may not provide sufficient di-electric strength or electric or heat resistive properties for insulation layers on an RF guidewire.

More specifically, the inventors of the present invention have invented a novel hydrophilic RF guidewire that overcomes the advantages of prior art mechanical guidewires. The novel RF guidewire in accordance with an embodiment of the present invention, provides an insulation layer that enables a hydrophilic coating to be disposed thereon. As such, some embodiments of the present invention provide a novel architecture for an insulation layer that uses a combination of materials that achieve chemical compatibility with a hydrophilic coating in addition to the mechanical, electrical and thermal properties for the RF guidewire.

The RF guidewire in accordance with some embodiments of the present invention provides several advantages corresponding to the aforementioned problems:
(a) The RF guidewire provides an insulation layer that enables a hydrophilic coating to be disposed thereon to reduce friction and enables the device to be inserted and advanced more smoothly through vasculature;
(b) The insulation layer provides sufficient heat resistance to enable the RF guidewire to withstand the heat produced from RF delivery, and additionally provides sufficient electrical resistivity to minimize leakage current to enhance patient safety; and
(c) The insulation layer provides these heat and electric resistive properties to enable RF delivery substantially without compromising the mechanical flexibility of the RF guidewire allowing the RF guidewire to navigate through vascular anatomy to enable the guidewire to reach the intended target location.

In one broad aspect, embodiments of the present invention provide an electrosurgical device for creating a channel through a region of tissue using energy provided by an electrical energy source, the electrosurgical device comprising: a core wire for receiving the energy from the electrical energy source; an electrode tip provided at a distal end of the core wire for delivery of the energy to the region of tissue, the electrode tip being electrically coupled to the core wire; an electrical insulation surrounding the core wire, the electrical insulation comprising at least one inner insulation layer and at least one outer insulation layer; a hydrophilic coating applied to an outer most insulation layer of the at least one outer insulation layer; and an electrically insulative thermal shield disposed between a proximal end of the electrode tip and the electrical insulation for thermally protecting the electrical insulation from heat produced by the delivery of the energy through the electrode tip.

As still another feature of this broad aspect, the at least one inner insulation layer comprises one or more inner polymer layers and wherein the at least one outer insulation layer comprises one or more outer polymer layers.

In some such embodiments, the at least one inner insulation layer comprises an electrically resistive inner insulation layer in contact with the core wire along a length of the core wire. In one specific embodiment, the electrically resistive inner insulation layer comprises a polymer defining an electrically resistive inner polymer layer.

In one such example, the electrically resistive inner polymer layer has a di-electric constant that is greater than the di-electric constant of the one or more outer polymer layers. In another such example the electrically resistive inner polymer layer has a width that is less than the width of the one or more outer insulation layers.

In still another such example the electrical insulation comprises:
a proximal insulation segment, the proximal insulation segment comprising the electrically resistive inner polymer layer and a substantially rigid outer polymer layer that surrounds the electrically resistive inner polymer layer, the proximal insulation segment being substantially rigid for allowing for pushability and torquability;
an intermediate insulation segment, wherein the intermediate insulation segment comprises the electrically resistive inner polymer layer, a substantially rigid outer polymer layer surrounding the electrically resistive inner polymer layer partially along a radial width of the electrosurgical device, a substantially flexible outer polymer layer surrounding the electrically resistive inner polymer layer partially along a radial width of the electrosurgical device, the intermediate insulation segment being more flexible than the proximal insulation segment to allow the electrosurgical device to be advanced through tortuous vasculature; and
a distal insulation segment comprising a thermal barrier for protecting the intermediate and proximal insulation segments from the delivery of energy from the electrode tip and the heat produced thereby; and
a hydrophilic coating disposed along the substantially rigid outer polymer layer along the proximal insulation segment and the substantially flexible outer polymer layer along the intermediate insulation segment; wherein the substantially rigid outer polymer layer along the proximal insulation segment and the substantially flexible outer polymer layer along the intermediate insulation segment, enable the hydrophilic coating to be disposed thereon.

In one example of this embodiment, the hydrophilic coating is selected from the group consisting of or comprising of: hyaluronic acid (HA), and a hydrogel. In a specific example of this embodiment, the hydrogel selected from the group consisting of or comprising of: polyvinylpyrrolidone (PVP), poly (ethylene oxide) (PEO) or poly (ethylene glycol) (PEG).

In another example of this embodiment, an area where the distal and intermediate insulation segments meet forms a joint where the substantially flexible outer polymer layer of the intermediate insulation segment overlaps and is positioned over the thermal barrier of the distal insulation segment.

In another example of this embodiment, an area where the distal and intermediate insulation segments meet forms a joint where thermal barrier of the distal insulation segment overlaps and is positioned over the substantially flexible outer polymer layer of the intermediate insulation segment.

As another feature of this broad aspect, the outer most insulation layer comprises a non-fluorinated polymer. In some such embodiments the outer most insulation layer is selected from the group consisting of or comprising of: polyimide, polyamide-imide, and polyether ether ketone (PEEK), polyurethane, nylon, polypropylene, silicone, polyether block amide, and (High Density Poly Ethylene) HDPE.

As another feature of this broad aspect, the at least one inner insulation layer and the at least one outer insulation layer, other than the outer most insulation layer, are selected from the group consisting of or comprising of: polyimide, polyamide-imide, and polyether ether ketone (PEEK), polytetrafluoroethylene (PTFE), Polyethylene terephthalate (PET) polyurethane, nylon, polypropylene, silicone, polyether block amide, and HDPE.

As a feature of this broad aspect, the electrosurgical device further comprises a support structure for supporting the electrode tip, the support structure having a proximal end, wherein the proximal end of the support structure is positioned distally with respect to a distal end of the electrically insulative thermal shield.

In one such embodiment, the electrically insulative thermal shield comprises a reverse taper such that the thermal shield that is wider along a distal portion of the thermal shield than along a proximal portion of the thermal shield, the electrical insulation being formed around the proximal portion of the thermal shield and providing a smooth transition between the thermal shield and the electrical insulation. In one such example, the thermal shield comprises a ceramic thermal shield. In a specific instance of this example, the ceramic thermal shield is tubular.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

As an overview of embodiments of the present invention, the RF guidewire provides an insulation layer that is amenable to having a hydrophilic coating disposed thereon substantially without impacting the mechanical properties of the RF guidewire while providing sufficient heat and electrical resistivity for protecting the RF guidewire from the RF delivery at the distal tip. As noted previously, mechanical guidewires that comprise a hydrophilic coating may comprise a polymer layer that is designed to provide sufficient mechanical flexibility, however, these polymers may not provide sufficient di-electric strength or the electric or heat resistive properties for insulation layers on RF guidewires. Furthermore, polymers that may have a sufficiently high di-electric strength or di-electric properties for an RF guidewire may be substantially rigid and may increase the stiffness of a guidewire beyond what is appropriate for the guidewire.

Details provided herein below with reference to FIGS. 2A-2B, include several embodiments of an RF guidewire. The disclosure will focus on the architecture of the insulation layer on the RF guidewire and the advantages offered thereby in terms of mechanical flexibility, heat and electrical resistivity, and compatibility with a hydrophilic coating.

RF Guidewire

Figure 1B:
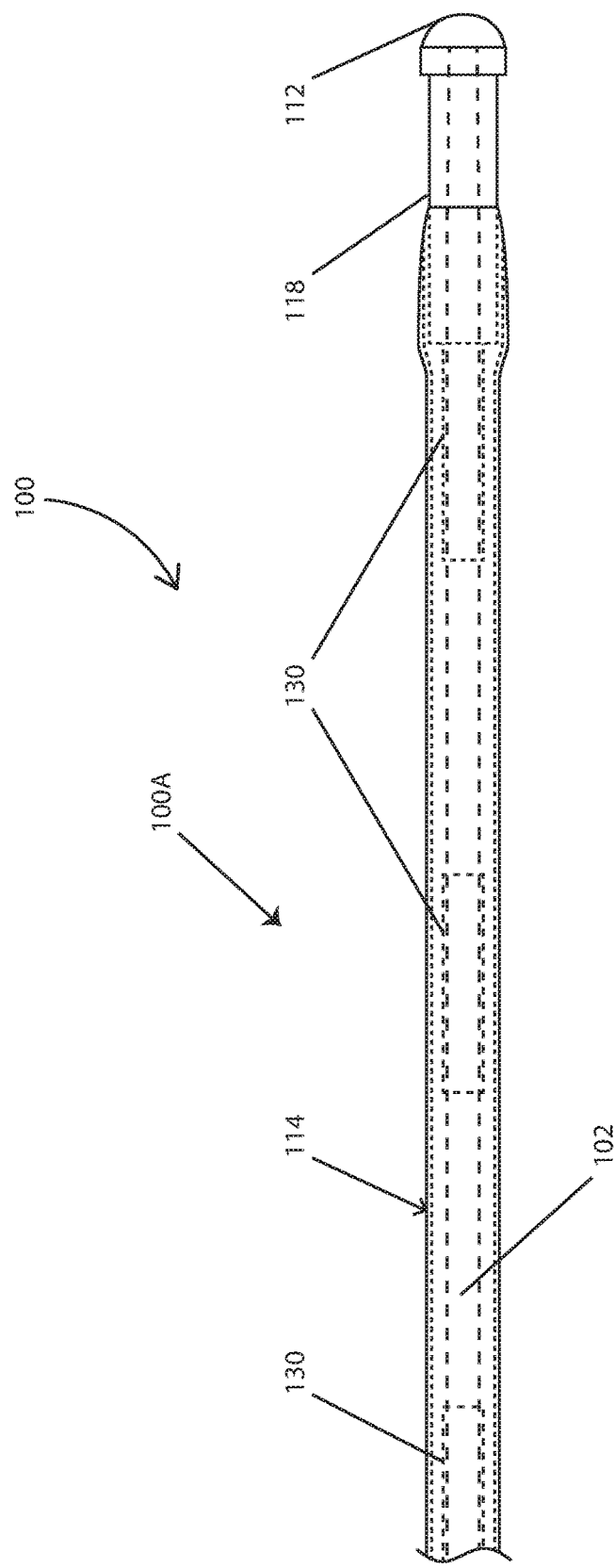

Firstly, a general overview of the structure of an RF guidewire is provided as illustrated in FIGS. 1A-1B, and as described herein below. This disclosure is followed a general overview of the insulation coating and a hydrophilic coating thereon, also shown in FIGS. 1A and 1B. A detailed overview of a further example of a hydrophilic RF guidewire and the architecture of the insulation coating, is then shown and described with reference to FIGS. 2A-2B, and 3A-3C.

The description provided herein below for electrosurgical device or energy delivery apparatus 100 should be understood by a person skilled in the art to apply to any one of the devices 100A-100F illustrated in the accompanying figures, unless otherwise indicated.

In accordance with an embodiment of the present invention, as shown in FIG. 1A, an electrosurgical device 100A is provided. The electrosurgical device comprises an inner elongate member 102 (also referred to generally as an "elongate member") which is an electrical conductor. A thermal shield 118 is positioned at the distal end of the elongate member. An electrode tip 112 is coupled to the distal end of the elongate member 102 distal to the thermal shield 118. In some embodiments, a support structure 120 is positioned distal to the thermal shield 118 for supporting the electrode tip 112. The elongate member has an insulation layer 114 disposed along a portion thereof including along a proximal region 106 of the device. The device proximal region is the portion of the device 100 that is proximal to the heat shield 118.

The inner elongate member 102 extends longitudinally and has a proximal end operable to be coupled to an energy source (not shown in the drawings) and a distal end coupled to an energy delivery component, such as an electrode having an electrode tip 112. In one embodiment, the inner elongate member or electrical conductor 102 may comprise a core wire. In one example, the core wire 202 may comprise a shape memory alloy, such as a nickel-titanium alloy. One example of a nickel-titanium alloy is Nitinol™. In another example, the core wire 202 may comprise stainless steel. Alternatively, any other suitable material may be used for core wire 202. In some embodiments the elongate member 102 may have an outer profile defined by a uniform or constant outer diameter along its length. In other embodiments, the elongate member 102 may have a variable outer diameter along its length. In some examples, the core wire has varying outer diameters along its length as shown by core wires 202a-202c in FIGS. 7A-7C. This may provide varying degrees of stiffness and flexibility along different sections of the core wire 202. The varying diameters of the core wire 202 and the thickness of the insulation layer 114 along the distal region of the device can help control/modify the stiffness of the device distal region. A smaller outer diameter in a section of the core wire 202 may provide increased flexibility of the wire in that region and may allow the wire to be floppier in that region. In one example, the core wire 202 has sufficient flexibility to allow the device 100 to conform to the vasculature of a patient and has sufficient rigidity to allow pushability of the device 100 through tissue. Alternatively, the elongate member 102 may have any other suitable profile. In one example, the elongate member 102 comprises a solid electrical conductor, to allow for increased rigidity. In another example, the elongate member 102 may be substantially hollow.

In some embodiments of the present invention the electrosurgical device 100 may have a predefined curvature. A portion of the electrosurgical device such as distal region 104 can be provided with varying degrees of curvature which may help in navigation of the device 100 through vasculature. In one example, the curvature of the electrosurgical device 100 may facilitate the device 100 engaging with an occlusion located in peripheral vasculature. In one specific example, the curvature of the electrosurgical device 100 may allow the device 100 to engage an occlusion located at or near a bifurcation in a body vessel. In some embodiments, the curvature of device 100 may be provided by fabricating the elongate member 102 from a shape memory alloy that has been shape-set to a preset curvature. In one example, the elongate member 102 may comprise a Nitinol wire which may be shape set with the specific angle of curvature or shape that is needed. In embodiments where a shape memory alloy such as Nitinol wire is used, the shape memory alloy can be treated to have super-elastic properties so that it will not deform permanently when it is pushed against an occlusion. The wire will this revert to its original shape when it is retracted minimizing the risk of the wire distal end being bent out of shape. In other embodiments, the elongate member 102 may have a bend or angle at a location along its length. In still other embodiments, the elongate member 102 may comprise a hollow hypotube such as a metal hypotube that may be laser cut to provide flexibility at the distal tip. In still other embodiments the core wire 202 may comprise a coil disposed onto a distal portion of the core wire 202 in order to increase flexibility in the distal portion. Furthermore, the device 100 may be a steerable device.

Insulation Layer

In some embodiments, the electrosurgical device 100 may have an insulation layer 114 disposed along a portion of the device 100, such that the insulation layer 114 substantially surrounds the elongate member 102 to minimize leakage of energy along elongate member 102. It should be understood that the term 'surrounds' as used herein can indicate, for example, that the insulation is applied directly to the elongate member or, as another example, that the insulation is applied to some intermediate layer located on the elongate member. In some embodiments the insulation layer 114 is disposed along a majority of the length of the device including along a proximal region 106 of the device. In other embodiments, the insulation layer 114 may be disposed substantially only along the proximal region 106 of the device. The insulation layer 114 helps to electrically insulate a portion of the electrosurgical device 100. This may help protect the patient and the user, for example the physician, from exposure to electrical current during use of device 100. In one example, the insulation layer 114 is disposed onto a core wire 202 of device 100, substantially along a proximal region of device 100. In one embodiment, the insulation layer is disposed onto the elongate member 102 after the distal components, comprising the thermal shield 118, the electrode tip 112 and/or support structure 120, have been coupled to or formed onto the elongate member 102 distal end. In other embodiments, the elongate member 102 may be coated with an insulation layer 114 prior to the distal components being coupled to the elongate member distal end. In other words, the elongate member 102 may be provided as an insulated elongate member 102 having an insulation layer 114. In one such example, the thermal shield 118 may be loaded onto a distal end of an insulated core wire 202 that is at least partially insulated. A support structure 120 may be loaded onto the core wire 202 and may be electrically in contact therewith, the support structure 120 being positioned distal to the thermal shield 118. Additionally, an electrode tip 112 may be formed integrally with the core wire 202 onto the support structure 120 as described further herein-below. In still other embodiments, the elongate member 102 may be provided as an insulated core wire 202 which can be coated with an additional insulation layer 114 after distal components have been coupled to the core wire 202 distal end.

A variety of materials may be used for the insulation layer 114, including but not limited to polymer or ceramic. A polymer insulation layer 114 may be provided using a heat shrink process or a melt processing method. Alternatively any other suitable method may be used. In some embodiments, the insulation layer 114 may be provided through a dip coating process. A portion of the electrosurgical device 100 or the elongate member 102 may be dipped in a liquid for e.g. a liquid polymer such as liquid PTFE or a ceramic. In other embodiments, a portion of the device 100 or the elongate member 102 may be spray coated with an insulative material for e.g. a polymer or a ceramic. In still other embodiments, a vapor deposition technique may be used to form the insulation layer 114. In some embodiments, where an insulated elongate member 102 is provided, the elongate member 102 may be dip coated with a polymer or insulated with a thin PTFE layer to form the insulated elongate member 102.

In one embodiment, a polymer combination may be used for the insulation layer 114. As an example, a two layer heat shrink layer may be used comprising an inner polymer layer 115 (which in some examples may be referred to as the second electrically insulating material or layer) and an outer polymer layer 117 (which in some examples may be referred to as the first electrically insulating material or layer). In another example, the inner polymer layer 115 may comprise a melt-processable polymer that can flow around and into any irregularities on the surface of core wire 202 and the outer polymer layer 117 may comprise a heat recoverable polymer. In a specific instance of this example, the insulation layer 114 comprises a combination of FEP and PTFE polymers, where the inner polymer layer 115 comprises FEP and the outer polymer layer 117 comprise PTFE as shown in FIG. 1A. A process combining re-flow and heat-shrink is used and the dual polymer layer is heated to a temperature of about 660° F., allowing the inner FEP layer to flow around and encapsulate the one or more radiopaque bands 130 disposed on core wire 202. Whereas, the outer PTFE layer recovers to a pre-specified diameter around the FEP and provides a smooth outer finish. In another instance of this example, PEBAX may be used as a melt-processable inner polymer layer. In one embodiment, one or more radiopaque bands 130 may be disposed along the core wire 202. The radiopaque bands 130 may comprise, for example, radiopaque material such as gold, iridium or platinum. In one example, a plurality of platinum radiopaque bands 130, are disposed along the core wire 202, as shown in FIG. 1B. In one embodiment, the insulation layer 114 may be disposed over the radiopaque bands 130. The insulation layer 114 may provide a smooth outer profile for the electrosurgical device 100.

Hydrophilic Coating

In one embodiment of the present invention, a portion of the electrosurgical device 100 may have a hydrophilic coating disposed thereon. This may help make the device lubricious and may help the device 100 to traverse through vasculature or through tissue, for e.g. an occlusion. The insulation layer 114 may comprise a material that allows a hydrophilic coating to be disposed thereon. In some embodiments the insulation layer 114 may comprise a polymer such as PEBAX, FEP or other non-fluoropolymers onto which a hydrophilic coating can be applied. In some embodiments, as mentioned previously, a combination of polymer layers may be used to form the insulation layer 114, for e.g. an inner polymer layer 115 and an outer polymer layer 117. In other examples, any number or combination of polymer layers may be possible. In such embodiments, the outer polymer layer may comprise a material that can be coated with a hydrophilic coating. Some non-limiting examples include an inner polymer layer 115 of PTFE and an outer polymer layer 117 of either FEP or Pebax, or an inner polymer layer 115 of FEP and an outer layer of Pebax. In some embodiments, the inner polymer layer 115 may provide electrical insulation and the outer polymer layer 117 may allow the device 100 to be coated with a hydrophilic coating. In some embodiments, entire device 100 may be coated with a hydrophilic coating. In other embodiments, the distal region 104 of the device 100 may have the hydrophilic coating which may include the thermal shield In other words, the distal region 104 may be made lubricious. In a non-limiting example, the hydrophilic coating may comprise Hyaluronic Acid (HA). Alternatively, the coating may also be a hydrophilic synthetic polymer based coating such as polyvinylpyrrolidone (PVP), poly (ethylene oxide) (PEO), poly (ethylene glycol) (PEG). These coatings are classified as hydrogels. Still furthermore, any other suitable hydrogel coating or any other hydrophilic coating may be used.

Example 1

Hydrophilic RF Guidewire

In one example, the present invention provides an electrosurgical device 100 for creating a channel through a region of tissue within a patient's body. More specifically, the electrosurgical device 100 comprises a novel hydrophilic RF guidewire 100F. Details of the novel hydrophilic guidewire 100F are provided herein below that provides a novel architecture for an insulation layer 114 for the RF guidewire 100F. The RF guidewire 100F overcomes the disadvantages of mechanical guidewires while providing an insulation layer that is amenable to having a hydrophilic coating disposed thereon, while maintaining both its electrical and heat resistive properties as well as mechanical properties including stiffness and flexibility along varying sections of the RF guidewire.

Device Architecture

Figure 2A:
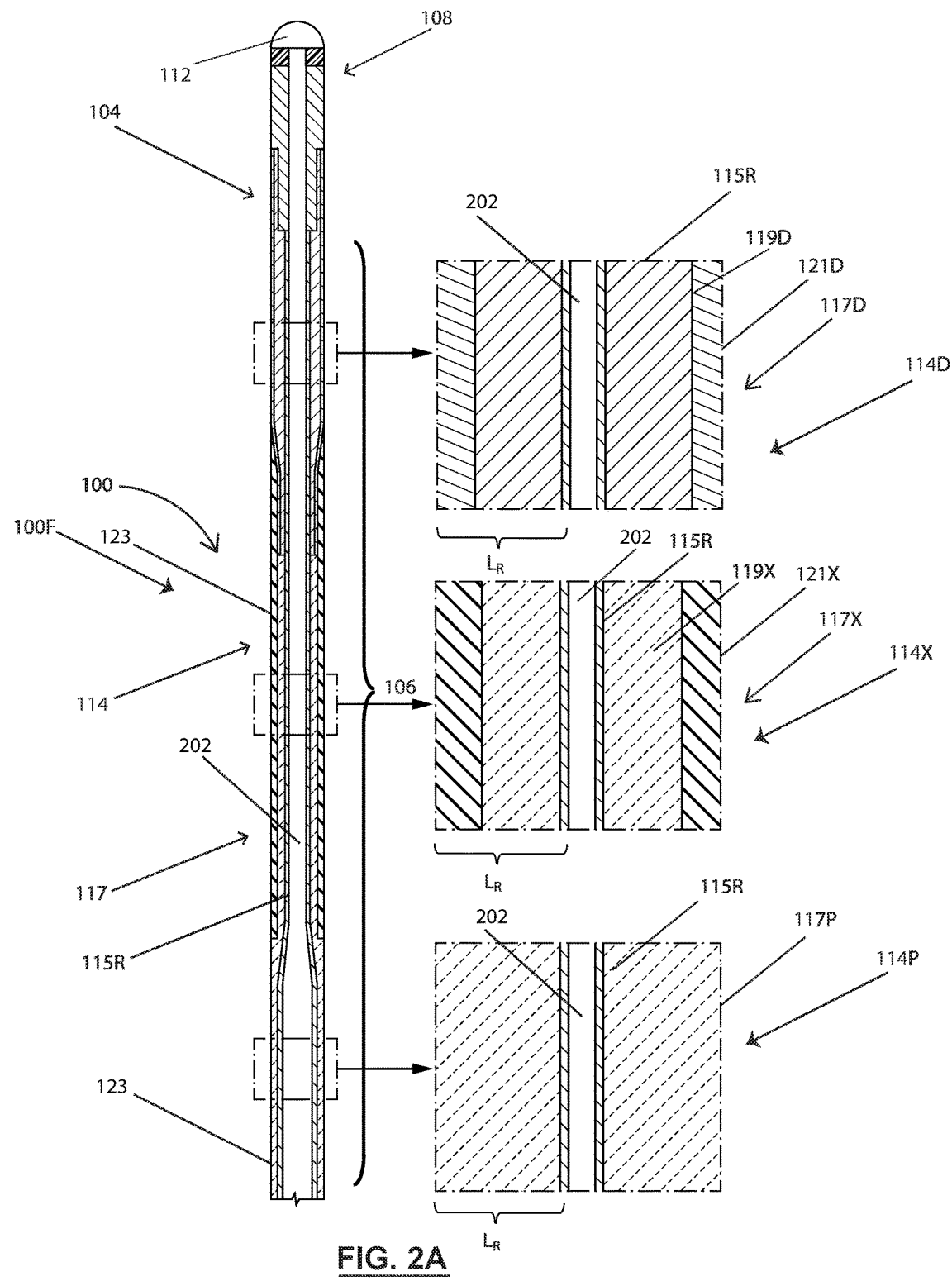
FIG. 2A-2B is an illustration of an electrosurgical device in accordance with an alternate embodiment of the present invention illustrating a novel architecture for an insulation layer.
Figure 2B:
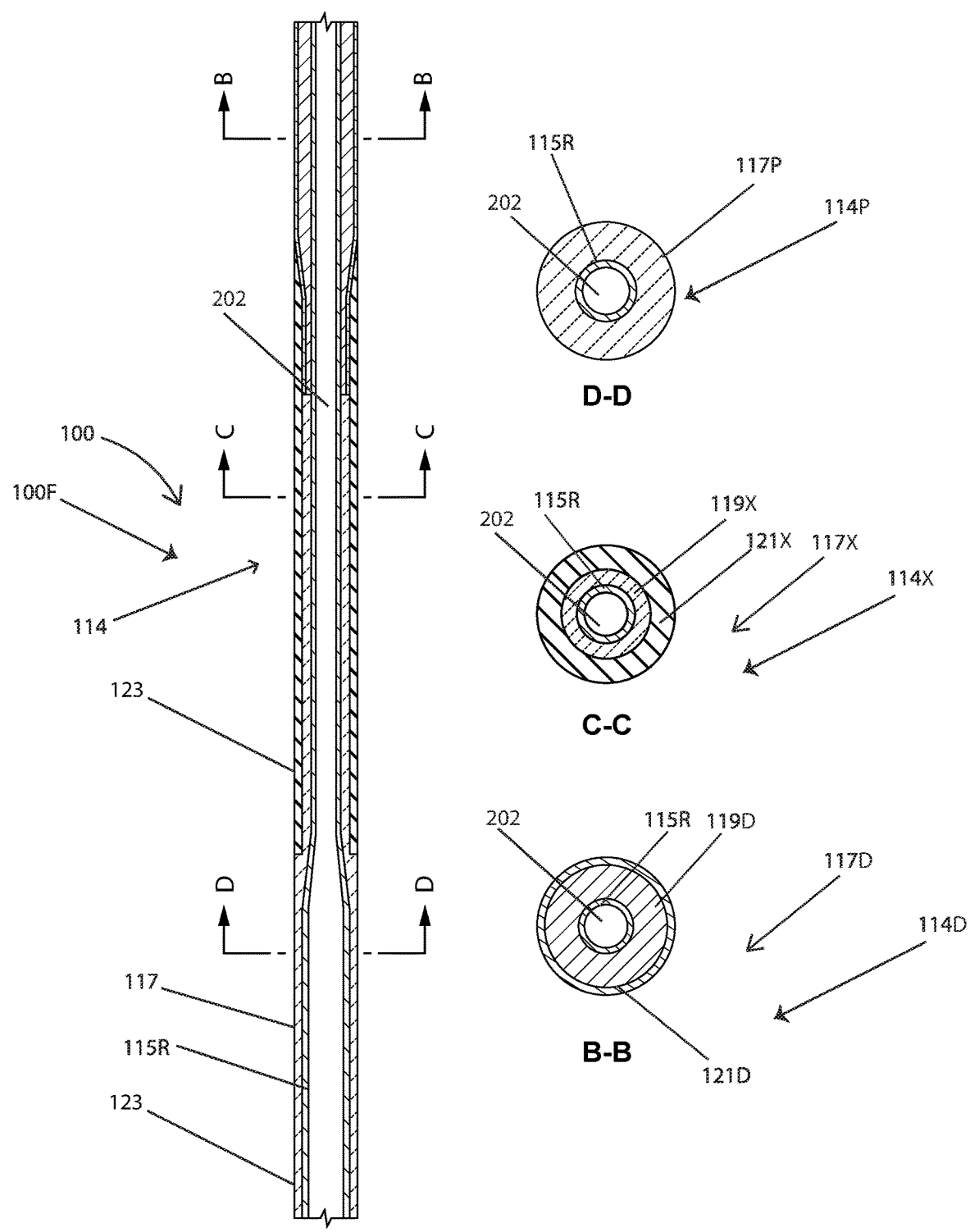

In one such example, as illustrated in FIGS. 2A-2B, the RF guidewire 100F comprises an insulation layer 114 with a novel architecture. The insulation layer 114 extends along the device proximal region 106. More specifically, the insulation layer 114 comprises three sections: a proximal insulation segment 114P, an intermediate insulation segment 114X, and a distal insulation segment 114D. In combination, the respective sections allow the mechanical properties of the RF guidewire 100F to be maintained while providing sufficient electrical and heat resistivity enabling it to function as a thermal and electrical insulator and while allowing the RF guidewire to be coated with a hydrophilic coating. As such, embodiments of the present invention provide a novel architecture for an insulation layer that satisfies the mechanical, thermal and electrical properties while being compatible with a hydrophilic coating.

First Component of the Insulation Layer

A first component of the insulation layer architecture comprises a thin electrically resistive or insulative inner layer 115R to help minimize leakage current. In one embodiment as shown in FIGS. 2A-2B, the RF guidewire 100F comprises an electrically conductive elongate member 102 comprising a core wire 202. The core wire 202 is coated with a thin film of a material having a high electrical resistance forming an electrically resistive or insulative inner insulation layer 115R that extends along the length of the core wire 202, along the proximal region 106 of the RF guidewire 100F. As such, the electrically resistive inner insulation layer 115R extends through the proximal, intermediate and distal segments (114P, 114X and 114D) of the insulation layer 114. In some such embodiments, the electrically resistive inner insulation layer 115R may comprise a polymer with a high-dielectric strength. In some such examples the electrically resistive inner insulation layer 115R may be referred to as the electrically resistive inner polymer layer 115R. In one example, the electrically resistive inner insulation layer (such as an electrically resistive inner polymer layer) has a di-electric constant that is greater than the di-electric constant of one or more outer insulation layers (such as one or more outer polymer layers). Still furthermore, in some examples the electrically resistive inner insulation layer (such as an electrically resistive inner polymer layer) has a width that is less than the width of the one or more outer insulation layers (such as one or more outer polymer layers).

Referring again to FIGS. 2A-2B, the electrically resistive inner layer 115R may surround the core wire 202, substantially along the length of the core wire 202. In a particular instance of this example, the electrically resistive inner insulation layer 115R comprises a polyimide coating that is applied on a tapered Nitinol™ core wire 202 (which in a particular example, may be one of the core wires 202 shown in FIGS. 7A-7C). The polyimide coating has a high di-electric strength and facilitates in minimizing current leakage. In one specific example, the polyimide coating has a radial thickness or length $L_R$ of at least about 0.001". In a specific instance of this example, the polyimide coating has a radial length or thickness of about 0.015". In some examples, the thickness of the insulation layer ranges from about 0.001" to about 0.030". In a more specific example, the range may be from about 0.005" to about 0.025". In some such examples, the core wire 202 may be built up to a 0.035" diameter. In other words, the RF guidewire 100F may have an outer diameter of about 0.035" where one or more additional insulation layers are applied on top of the polyimide layer along the respective, proximal, intermediate and distal insulation segments (114P, 114X and 114D). In other examples, the polyimide coating may have any other thickness that provides electrical insulation substantially without increasing the mechanical stiffness of the RF guidewire 100F. In other examples, the thin electrically resistive inner insulation layer may comprise any other suitable polymer such as polyamide-imide or polyether ether ketone (PEEK). In some such embodiments, the inner electrically resistive inner polymer layer 115R comprises a non-fluorinated polymer. Alternatively, the inner electrically resistive inner insulation layer 115R may comprise a fluorinated polymer such as polytetrafluoroethylene (PTFE), fluorinated ethylene propylene (FEP) and Polyethylene terephthalate (PET). Similarly, an outer insulation layer 117P that is provided around the inner insulation layer 115R may comprise one or more layers as outlined further herein below. In some such embodiments, for layers other than the outer most layer of the outer insulation layer, a non-fluorinated polymer or a fluorinated polymer may be used. Thus, in some examples the electrically resistive inner insulation layer 115R may comprise a fluorinated or non-fluorinated polymer, examples of such polymers are provided in the disclosure herein below.

Second Component of the Insulation Layer

Furthermore, some embodiments of the present invention provide an outermost insulation layer substantially along the length of the RF guidewire 100F that enables a hydrophilic coating to be disposed thereon. Specifically, the RF guidewire 100F comprises one or more outer insulation layers where the outer most insulation layer comprises a hydrophilic coating along a substantial portion of the RF guidewire 100F. Details of the one or more outer insulation layers are provided herein below including the outer most insulation layer. In some embodiments of present invention, a heat resistive material may be provided for outer surface of the insulation layer (or in other words the outermost insulation layer) adjacent to the distal region 104 [which includes the heat shield 118], for example along the distal insulation segment 114D. In some such examples, the heat resistive material may not comprise a hydrophilic coating disposed along it or may not be compatible with a hydrophilic coating.

Proximal Insulation Segment

In some embodiments, a substantially rigid proximal insulation segment 114P is provided.

More specifically, the proximal end of the RF guidewire 100F is clad in a substantially rigid outer insulation layer 117P along the proximal insulation segment 114P. In some such examples, this may comprise a polymer layer. The substantially rigid outer polymer layer 117P is applied on top of the electrically resistive inner insulation layer 115R. This material provides suitable mechanical stiffness and pushability for the proximal end of the RF guidewire 100F. The substantially rigid outer polymer layer 117P additionally provides for good dielectric strength and high electrical resistivity to prevent current leakage. As such, the substantially rigid outer polymer layer 117P in conjunction/combination with the electrically resistive inner polymer layer 115R functions to further prevent current leakage, while providing mechanical stiffness. In some examples, the proximal insulation segment is substantially rigid or stiff for allowing for pushability and torquability of the RF guidewire 100F. The substantially rigid outer polymer layer 117P is additionally compatible with a hydrophilic coating, and thus enables a hydrophilic coating to be disposed thereon. As, such in some embodiments of the present invention, the substantially rigid outer polymer layer 117P forms the outer most insulation layer along the proximal insulation segment 114P and additionally comprises a hydrophilic coating 123 disposed along its outer most surface. As such in some examples, the substantially rigid outer polymer layer 117P along the proximal insulation segment 114P enables the hydrophilic coating 123 to be disposed thereon. As such, in some examples, the RF guidewire 100F has a hydrophilic coating disposed along the substantially rigid outer polymer layer 117P along the proximal insulation segment 114P.

In one such example, the substantially rigid outer polymer layer 117P comprises a (high density polyethylene) HDPE layer. In a specific instance of this example, the electrically resistive inner polymer layer 115R comprises polyimide. The polyimide layer and HDPE layers work together to provide the electrical resistivity and mechanical stiffness for the proximal end to minimize leakage current and to provide sufficient stiffness for torquability and pushability while maintaining sufficient mechanical flexibility of the RF guidewire 100F to enable ease of advancement through vasculature. Furthermore, the outer HDPE layer functions as a suitable substrate for permitting a hydrophilic coating to be disposed thereon. In one such example, the hydrophilic coating comprises hyaluronic acid [HA]. Alternatively, as outlined previously herein above, the coating may also be a hydrophilic synthetic polymer such as a hydrogel. Some examples may include: polyvinylpyrrolidone (PVP), poly (ethylene oxide) (PEO) or poly (ethylene glycol) (PEG). Still furthermore, any other hydrogel coating that may be suitable for application on an RF guidewire may be used.

Figure 7A:
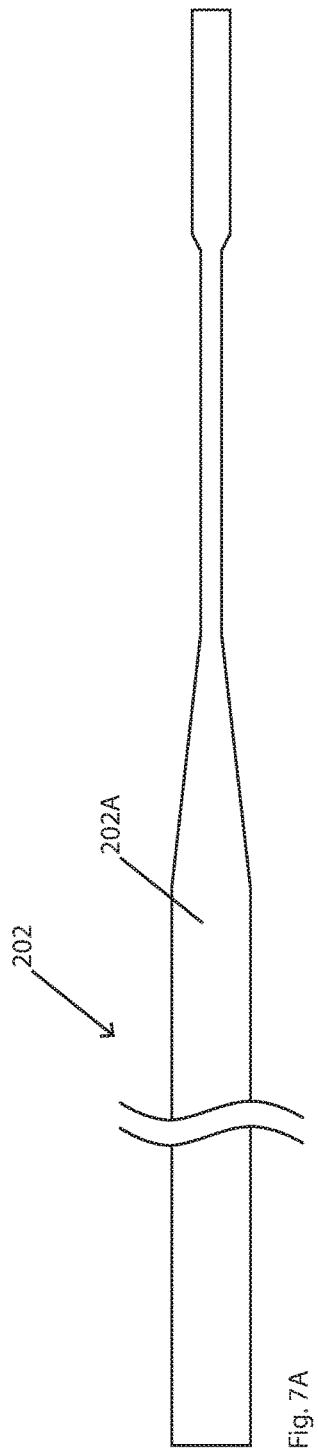
FIGS. 7A-7C show an elongate member of an electrosurgical device in accordance with various embodiments of the present invention.
Figure 7B:
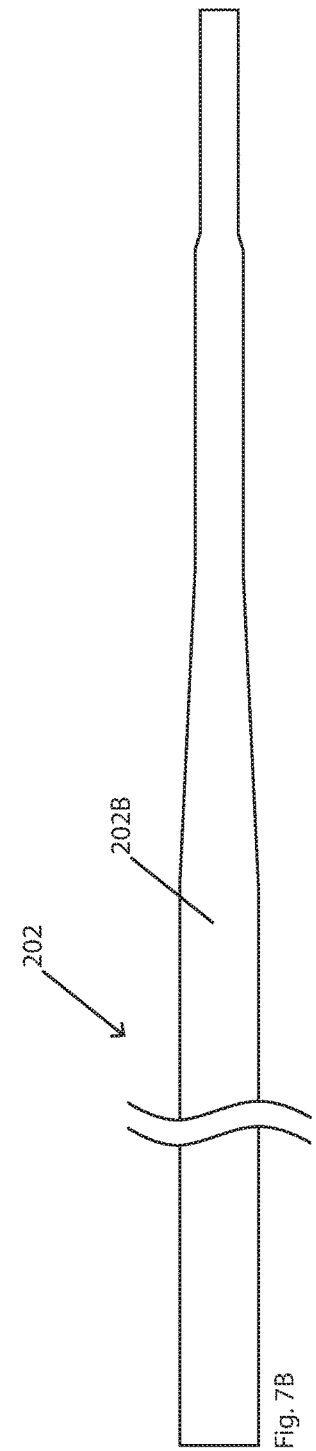
Figure 7C:
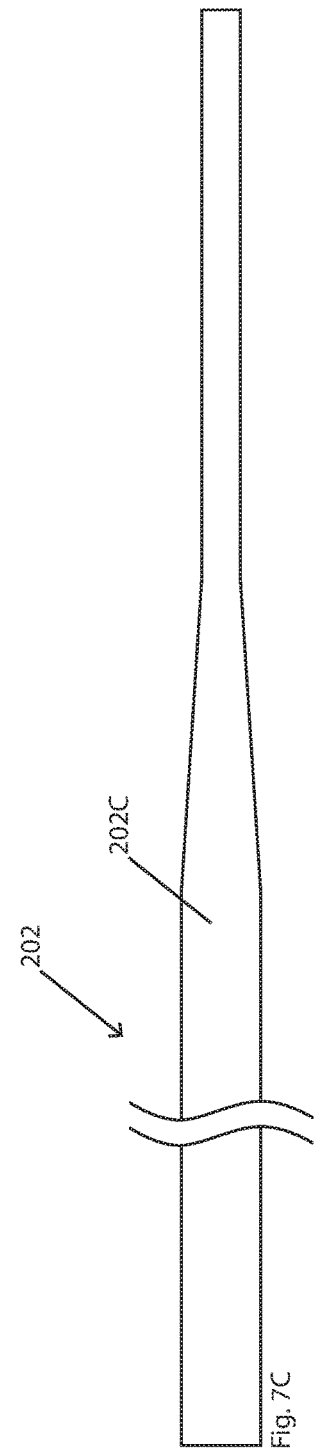

In a particular instance of the present embodiment, where the proximal insulation segment 114P comprises an inner insulation layer 115R comprising a polyimide and the outer insulation layer 117P comprising HDPE, the di-electric constant of the polyimide layer may be about 3.5 and the di-electric constant of the HDPE layer may be about 2.3. In a specific instance of this example, the polyimide coating has a radial length or thickness $L_R$ of about 0.015" and the RF guidewire is built to an outer diameter of about 0.035", with the HDPE layer forming the remainder of the radial thickness. In one example, the proximal insulation segment 114P extends for a length of about 240 cm along the longitudinal length of the core wire 202. In some such embodiments, the radial thickness $L_R$ of the outer HDPE layer may vary based on the type of core wire 202 utilized. As shown in FIGS. 7A-7C, in some such embodiments, the core wire 202 may have a variable diameter along its longitudinal length.

As such, along the proximal insulation segment 114P, the combination of the insulation layers, the relatively thin electrically insulative inner insulation layer 115R, in combination with a thicker substantially rigid outer insulation layer 117B that is compatible with a hydrophilic coating, provides the RF guidewire 100F with a substantially rigid proximal insulation segment 114P that gives the stiffness along the proximal portion to enable maneuverability and torquability while providing the electrical resistivity to prevent current leakage, while further enabling a hydrophilic coating to be disposed thereon.

Intermediate Insulation Segment

In some embodiments, of the present invention, the insulation layer 114 comprises a substantially flexible intermediate insulation segment 114X that extends from and is positioned distal to the substantially rigid proximal insulation segment 114P.

The distal portion of the wire is relatively more flexible. As such, a combination of outer insulation layers is provided to create adequate stiffness and electrical insulation. In a particular example, as outlined in further detail herein below, a mix of Pebax® and HDPE may be used to form the outer insulation layer 117X towards the distal portion of the RF guidewire 100F. In one such example, a substantially rigid outer insulation layer such as HDPE is provided along a portion of the radial length $L_R$ of the insulation layer 114. In one such example, HDPE may not be provided along the entire radial length $L_R$ of the RF guidewire so the RF guidewire may not be too stiff along the distal portion (which includes the section of the RF guidewire 100F along the intermediate insulation segment 114X).

Details of the substantially flexible intermediate insulation segment 114X are shown in FIGS. 2A-2B. The intermediate insulation segment 114X provides the RF guidewire 100F with sufficient flexibility to allow the RF guidewire 100F to be able to navigate through vasculature and tortuous anatomy and to facilitate the RF guidewire 100F in reaching the target anatomy. In order to provide greater flexibility in this segment, a substantially flexible outer insulation layer 117X is provided that surrounds the substantially rigid electrically insulative inner insulation layer 115R which in some examples may comprise a rigid electrically resistive or insulative inner polymer layer 115R.

In some such embodiments, the substantially flexible outer insulation layer 117X may be formed from a combination of insulation layers. As such, in a particular example, a first outer insulation layer 119X is provided that is substantially rigid or stiff, for example a polymer such as HDPE along a portion of the radial length of the intermediate insulation segment 114X. Having the HDPE extend along a portion of the radial length or width $L_R$ may help ensure that the RF guidewire 100F is not too stiff along the distal insulation segment 114D. In some such embodiments, the remaining radial width $L_R$ may comprise a second outer insulation layer 121X that may comprise a more flexible insulation layer. The second outer insulation layer 121X is additionally compatible with hydrophilic coatings and enables a hydrophilic coating to be disposed thereon. As, such in some embodiments of the present invention, the second outer insulation layer 121X (such as a substantially flexible outer polymer layer 121X) forms the outer most insulation layer along the intermediate insulation segment 114X and additionally comprises a hydrophilic coating 123 disposed along its outer most surface. As such the substantially flexible outer polymer layer 121X along the intermediate insulation segment 114X, enables the hydrophilic coating 123 to be disposed thereon.

In a specific instance, the first outer insulation layer 119X comprises a substantially rigid outer insulation layer (such as a substantially rigid outer polymer layer) for example an HDPE layer. The substantially rigid outer polymer layer 119X comprising HDPE is provided on top of the substantially rigid electrically insulative inner insulation layer 115R comprising polyimide. The HDPE layer has a thickness that is limited to about 0.016", and the remaining width of the insulation layer 114 is provided as a Pebax layer on top of the HDPE layer, where the Pebax layer defines the second outer insulation layer 121X. More specifically, the Pebax layer is used to build the wire to a 0.035" outer diameter on top of the HDPE layer. This may help ensure adequate electrical resistivity from HDPE, and proper mechanical stiffness and hydrophilic coating compatibility from the Pebax layer. In some embodiments, the intermediate insulation segment 114X has a length of about 5 cm.

As such, along the intermediate insulation segment 114X, the combination of the insulation layers, the relatively thin electrically insulative inner insulation layer 115R, in combination with a substantially flexible outer insulation layer 117X that is compatible with a hydrophilic coating, provides the RF guidewire 100F with several advantages. Specifically, the construct provides a substantially flexible intermediate insulation segment 114X that gives flexibility along the intermediate segment while providing electrical resistivity, while further enabling a hydrophilic coating to be disposed thereon. In some embodiments, the substantially flexible outer insulation layer 117X may comprise one or more outer insulation layers of varying rigidity.

Thus in some examples, outlined herein, the intermediate insulation segment 114X, comprises (i) the electrically resistive inner insulation layer 115R (which in some examples comprises an electrically resistive inner polymer layer), (ii) the first outer insulation layer 119X (which may be a substantially rigid outer polymer layer) surrounding the electrically resistive inner polymer layer partially along the radial width of the electrosurgical device, and (iii) a second outer insulation layer 121X (which may be a substantially flexible outer polymer layer 117X) surrounding the electrically resistive inner polymer layer partially along the radial width of the electrosurgical device, where the intermediate insulation segment 114X is more flexible than the proximal insulation segment 114P to allow the RF guidewire 100F to be advanced through tortuous vasculature. Furthermore, the substantially flexible outer polymer layer 121X along the intermediate insulation segment 114X, enables a hydrophilic coating to be disposed thereon. In some such examples, a hydrophilic coating is disposed along the substantially flexible outer polymer layer 121X along the intermediate insulation segment.

Distal Insulation Segment

A distal insulation segment 114D is provided that extends distally from the intermediate insulation segment 114X. The distal insulation segment 114D provides first and second outer insulation layers (119D, 121D) where the second outer insulation layer defines a secondary heat shield or thermal barrier 121D surrounding the electrically insulative inner insulation layer 115R. As such, the distal insulation segment 114D provides sufficient electrical resistance and functions to substantially thermally isolate or protect the intermediate and proximal insulation segments from heat generated at the distal tip 108 which includes the electrode tip 112. In one such example the thermal barrier 121D forms a part of the outer insulation layer 117D along the distal insulation segment 114D. An additional outer insulation layer 119D may also be provided in conjunction with the thermal barrier 121D that functions to provide heat resistive and electrical resistive properties in combination with the thermal barrier 121D to protect the proximal and intermediate insulation segments 114P, 114X from the heat and leakage current from the delivery of RF current from the distal region 104, specifically at the distal tip 108. As such the distal insulation segment 114D comprises a thermal barrier 121D for protecting the intermediate and proximal insulation segments (114X, 114P) from the delivery of energy from the electrode tip 112 and the heat produced thereby.

In a specific example, the thermal barrier or second outer insulation layer 121D comprises a PTFE segment that functions as a heat shield to prevent damage to the materials used in the intermediate and distal insulation segments (114D and 114X). Similar to embodiments discussed herein above, the first outer insulation layer 119D is provided underneath the thermal barrier 121D. In one such example, the first outer insulation layer 119D comprises fluorinated ethylene propylene (FEP). In other words, the PTFE layer defining the thermal barrier 121D is placed over the FEP layer defining the first outer insulation layer 119D along the distal insulation segment 114D. The FEP layer is provided over a polyimide coated core wire 202, where the polyimide coating forms the electrically resistive inner insulation layer 115R.

In one such example, the distal insulation segment 114D has a longitudinal length of about 1 cm, where the PTFE thermal barrier 121D extends for about 1 cm. As outlined herein below, the distal region 104 consists or comprises of the domed electrode tip 112 and a heat shield 118 which in some examples comprises a ceramic. During use, the electrode tip 112 may generate a large amount of heat during RF delivery for example to enable RF cutting. In order to prevent damage to the intermediate insulation segment 114X [specifically the second outer insulation layer 121X along the intermediate insulation segment 114X]], the thermal barrier 121D is extended from the proximal tip of the heat shield 118 to the intermediate insulation segment 114X material to provide a greater distance between it and the electrode tip 112. In the specific example discussed above, the PTFE thermal barrier 121D extends from the heat shield 118 to the intermediate insulation segment, in order to thermally protect the Pebax layer forming the second outer insulation layer 121X along the intermediate insulation segment 114X.

In the embodiments described herein above, the inner electrically resistive insulation layer 115R may comprise other polymers, in addition to polyimide, that provide high electrical resistivity such as polyamide-imide. Similarly, the outer insulation layers 117P, 119X of the proximal and intermediate insulation segments (114P, 114X), may comprise a material other than HDPE. For example, these segments may comprise other non-fluorinated polymers that possess similar properties to HDPE. Still furthermore, the second outer insulation layer 121X along the intermediate insulation segment 114X may comprise a material other than Pebax. For example, this layer may comprise other non-fluorinated polymers that possess similar properties as Pebax. In other embodiments, different durometers of Pebax may be used. In some such examples, alternative polymers for proximal and intermediate outer insulation layers could be different durometers of Pebax such as Pebax 72, 55 or 33, or alternatively one or more of the layers may comprise polyethylene terephthalate (PET). Still furthermore, the secondary heat shield 121D may comprise other polymers that exhibit high heat resistivity such as PEEK.

In some examples, the insulation layers along the proximal, intermediate and distal insulation segments (114P, 114X, 114D) that are other than the outer most insulation layer, may comprise a fluorinated or a non-fluorinated polymer. In some such examples, the outer most layer along the proximal and intermediate insulation segments 114P, 114X comprises a non-fluorinated polymer. In an alternate example, the outer most layer along the distal insulation segment 114D comprises a fluorinated polymer. In additional examples, the outer most layer along the distal insulation segment 114D may also comprise a non-fluorinated polymer.

Some examples of such non-fluorinated polymers include: polyurethane, nylon, polypropylene, and silicone, and PEEK, (PET), polyimide, polyamide-imide, Pebax such as Pebax 72, 55 or 33, HDPE as noted above. In examples where Pebax is used, any other polyether block amide or PEBA or block copolymer such as Pebax may be used, which comprise thermoplastic elastomer (TPE). Some examples of fluorinated polymers may include polytetrafluoroethylene (PTFE) and Polyethylene terephthalate (PET).

Overview of Examples 2A-2B

As such as outlined herein above, and as shown in FIGS. 2A-2B, in a specific example a tapered nitinol core wire 202 may be used to provide stiffness, superelasticity, and current conduction. The electrode may be provided as a domed electrode tip 112 which may provide controlled RF delivery. A polyimide coating may be applied on the nitinol core wire 202 to serve as an inner electrical insulator or electrically resistive inner insulation layer 115R for dielectric strength. In some examples this layer may be at least 0.001" thick to provide electrical resistivity to minimize current leakage. Alternatively, the polyimide layer thickness may be increased to improve electrical properties, but as polyimide is a relatively stiff material, the layer thickness may be increased while ensuring that RF guidewire remains substantially flexible such that is not too stiff. The next layer on top of the polyimide is HDPE which forms the outer insulation layer 117P in the proximal insulation segment 114P. The HDPE layer may fill the proximal end of the RF guidewire 100F and act as the substrate for the hydrophilic coating along the proximal insulation segment 114P. HDPE has good electrical properties and may additionally decrease the leakage current further to the base polyimide layer. Compared to some strong polymeric electrical insulators, it is also relatively soft so that the leakage current may be minimized while providing sufficient flexibility substantially without affecting the device's ability to navigate through vasculature. Furthermore, it is compatible with a hydrophilic coating.

In one such example, HDPE may be used to fill the proximal insulation segment 114P substantially along its length, whereas the distal 6 cm of the RF guidewire 100F remains soft and flexible (this includes the intermediate 114X and distal 114D insulation segments). In some examples, the distal sections of the RF guidewire 100F (which include the intermediate 114X and distal 114D segments) may not be completely filled with HDPE to minimize the distal section stiffness (along the intermediate and distal insulation segments 114P, 114X) such that it is not too high compared to the proximal insulation segment 114P. As such, in one example, along the intermediate insulation segment 114X, the HDPE layer forming the first outer insulation layer 119X is about 0.003" thick, and the rest of the shaft around the core wire 202 may be formed with a soft polyether block amide layer such as a Pebax layer, which may form the second outer insulation layer 121X. Pebax is compatible with hydrophilic coatings and is substantially soft at the same time. Alternatively, different durometers of the Pebax may be used to provide variable stiffness along distal sections of the RF guidewire 100F (which may include the intermediate and distal insulation segments (114X, 114D).

Furthermore, the distal region 108 includes a distal tip 104 defining a domed electrode tip 112, and a heat shield 118 that may comprise a ceramic heat shield 218 or 318. The electrode 112 at the distal tip 108 may generate a large amount of heat during RF delivery for example for RF cutting, and the heat shield 118 functions to protect the insulation layer 114 such as a polymer along the distal section of shaft by extending the distance between the RF delivery portion and the polymer materials.

As noted previously herein above and as described in further detail herein below, the heat shield 118 such as a ceramic heat shield 218 or 318 functions to isolate the heat and prevent heat damage to the insulation layer 114. However, in some embodiments, the second outer insulation layer 121X along the intermediate segment 114X may have a relatively low melting temperature, which for example may be lower than the melting temperature of the second outer insulation layer 121D along the distal insulation segment 114D. In the specific example discussed above, since Pebax is used along the shaft in the intermediate insulation segment 114X, the distance between the electrode tip 112 and the Pebax polymer layer along the intermediate insulation segment 114X is further extended as Pebax has as relatively low melting temperature, which is for example lower than PTFE. To achieve the extension, a second outer insulation layer 121D (or in other words a secondary heat shield or thermal barrier 121D) comprising PTFE is added along the distal insulation segment 114D, just proximal to the ceramic heat shield 118 to further isolate the heat from the Pebax material on the distal section of the shaft. In other words, the extension of distance between the dome of the electrode tip 112 and the second outer insulation segment 121X comprising Pebax is achieved by extending the length of the PTFE layer defining the thermal barrier 121D. In some such examples, the thermal barrier 121D that comprises PTFE may provide a substantially more flexible heat shield section than the substantially rigid ceramic heat shield section provided by the ceramic heat shield 118 at the distal region 104, which may facilitate the device or RF guidewire 100F to advance through tortuous paths.

Example 3A

Figure 3A:
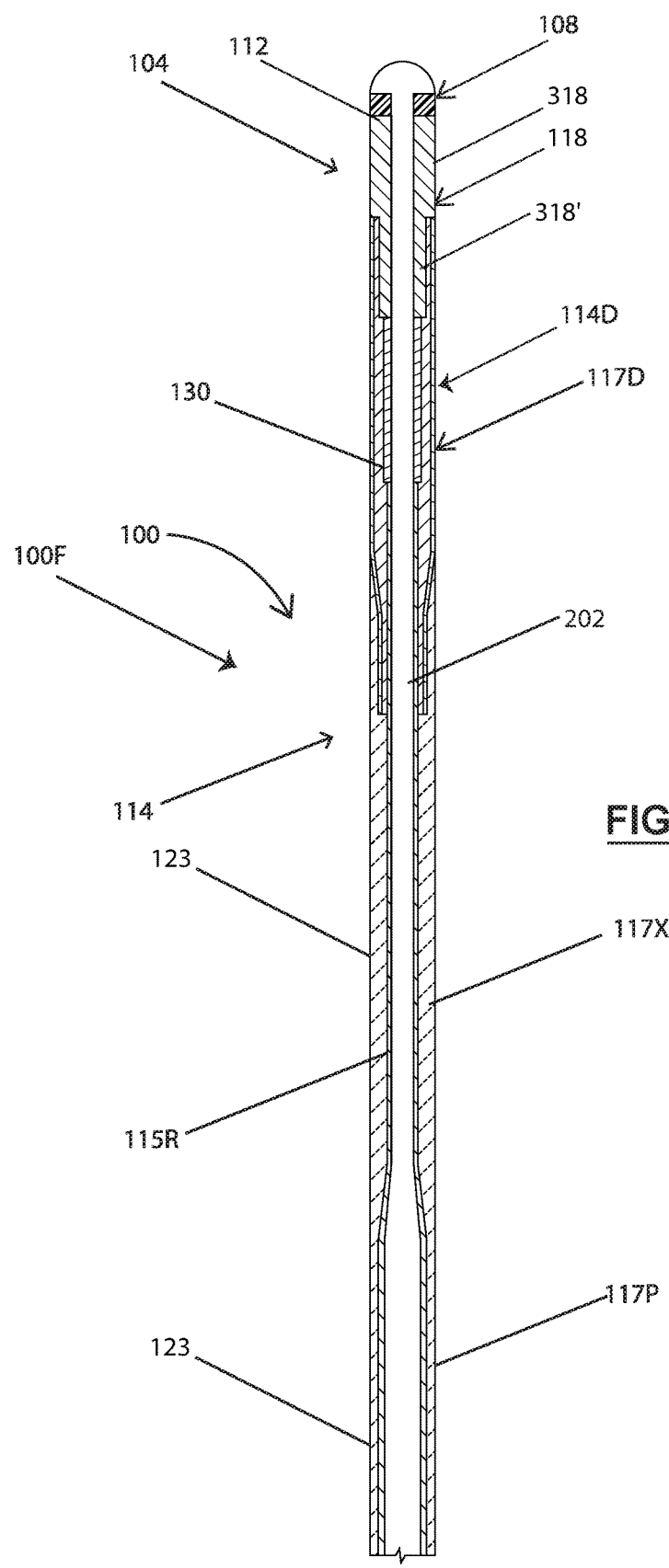

Another example of an RF guidewire 100F, having a novel architecture is shown in FIG. 3A. The RF guidewire comprises a distal region 104 and a proximal region 106. The distal region 104 comprises a tantalum support structure 120 comprising a tantalum puck, where the domed electrode tip 112 is formed onto the support structure]. The ceramic heat shield 318 is positioned proximal to the tantalum puck and a platinum marker 130 may be positioned proximal to the heat shield 318. This is further illustrated in FIG. 4B. A distal insulation segment or heat insulating layer or segment 114D comprising an outer insulation layer or heat insulative tip 117D that is provided proximal to the ceramic heat shield 318 that extends around the step-down portion of the ceramic heat shield 318. In other words, the electrically insulative thermal shield comprises a step-down thermal shield 318 that is wider along a distal portion of the thermal shield 318 than along a proximal portion of the thermal shield 318. In other words, the thermal shield 318 defines a reverse taper 318' such that the thermal shield is wider at its distal portion than along its proximal portion. As such, the electrical insulation or insulation layer 114 is formed around the proximal portion of the thermal shield 318 and provides a smooth transition between the thermal shield 318 and the insulation layer 114. In some such examples, the thermal shield 318 is a tubular ceramic.

Additionally, an outer insulation layer 117P, 117X is provided along the proximal and intermediate insulation segments (114P, 114X) that is compatible with a hydrophilic coating allowing a hydrophilic coating to be disposed thereon. The outer insulation layer 117P, 117X, and the heat insulating tip 117D are disposed over an electrically insulative inner insulation layer or coating 115R (for example a polyimide layer) which is formed over a tapered core wire 202. The electrically insulative inner insulation layer or coating 115R extends substantially along the length of the core wire 202 and may extend up to the heat shield 118 is some examples. In one example the polyimide layer extends till the platinum marker 130.

An overlap exists between the outer insulation layer 117D and the outer insulation layer 117X, at the junction between the intermediate insulation segment 114X and the distal insulation segment 114D, where one or more layers of the outer insulation layer 117X extend around one or more layers of the outer insulation layer 117D.

In some such examples, the heat insulative tip 117D comprises first and second outer insulation layers 119D, 121D, where the second outer insulation layer 121D defines a thermal barrier 121D, similar to embodiments described herein above with reference to FIGS. 2A and 2B. FIG. 3A illustrates an outer insulation layer 117X comprising a single outer layer. Alternatively, the outer insulation layer 117X may comprise inner and outer insulation layers 119X, 121X.

Examples 3B

In one example, as shown in FIG. 3B, the heat insulative tip 117D may consist of a thermal barrier 121D comprising a PTFE layer overtop a first outer insulation layer 119D comprising an FEP layer, which is applied over a polyimide tube that forms the electrically resistive inner polymer layer 115R, where the outer insulation layer 117X (or a portion thereof such as the second outer insulation layer 121X), along intermediate insulation segment 114X, overlaps the heat insulative tip 117D.

In some such embodiments, where PTFE and Pebax are used (for the thermal barrier 121D and the second outer insulation layer 121X, respectively), the two materials may overlap at the junction between the two segments (intermediate insulation segment 114X, distal insulation segment 114D). In some such embodiments, a joint structure may be provided between PTFE and Pebax to allow the two materials to bond together and minimize the risk of material flaring. In the example shown in FIG. 3B, the overlap joint may face the opposite direction to that shown in FIG. 2A (which illustrates the PTFE layer as being underneath the pebax, layer). In some examples, similar to the example shown in FIG. 3B, the PTFE layer may also overlap the pebax. More specifically, the Pebax layer forming the outer insulation layer 121X of the intermediate insulation segment 114X overlaps or extends over the proximal portion of the outer insulation layer 121D (which comprises the PTFE layer over an FEP layer) of the distal insulation segment 114D.

In some such examples, an overlap exists between one or more layers of the intermediate and distal insulation segments (114X, 114D). More specifically, an overlap exists between the second outer insulation layer 121X and the outer insulation layer or thermal barrier 121D. The second outer insulation layer 121X may be an outer polymer layer which may comprise a substantially flexible outer polymer layer. The thermal barrier 121D for example may also comprising an outer polymer layer. The area where the distal 114D and intermediate 114X insulation segments meet forms a joint. Specifically the area where the substantially flexible outer polymer layer 121X and the thermal barrier 121D meet forms a joint where the thermal barrier 121D of the distal insulation segment 114D overlaps and is positioned over the substantially flexible outer polymer layer 121X of the intermediate insulation segment 114X.

Alternatively, a butt joint may be possible between the Pebax and the PTFE layers. Still furthermore, glue may also be used to join the two layers (Pebax, PTFE).

Example 3C

Figure 3C:
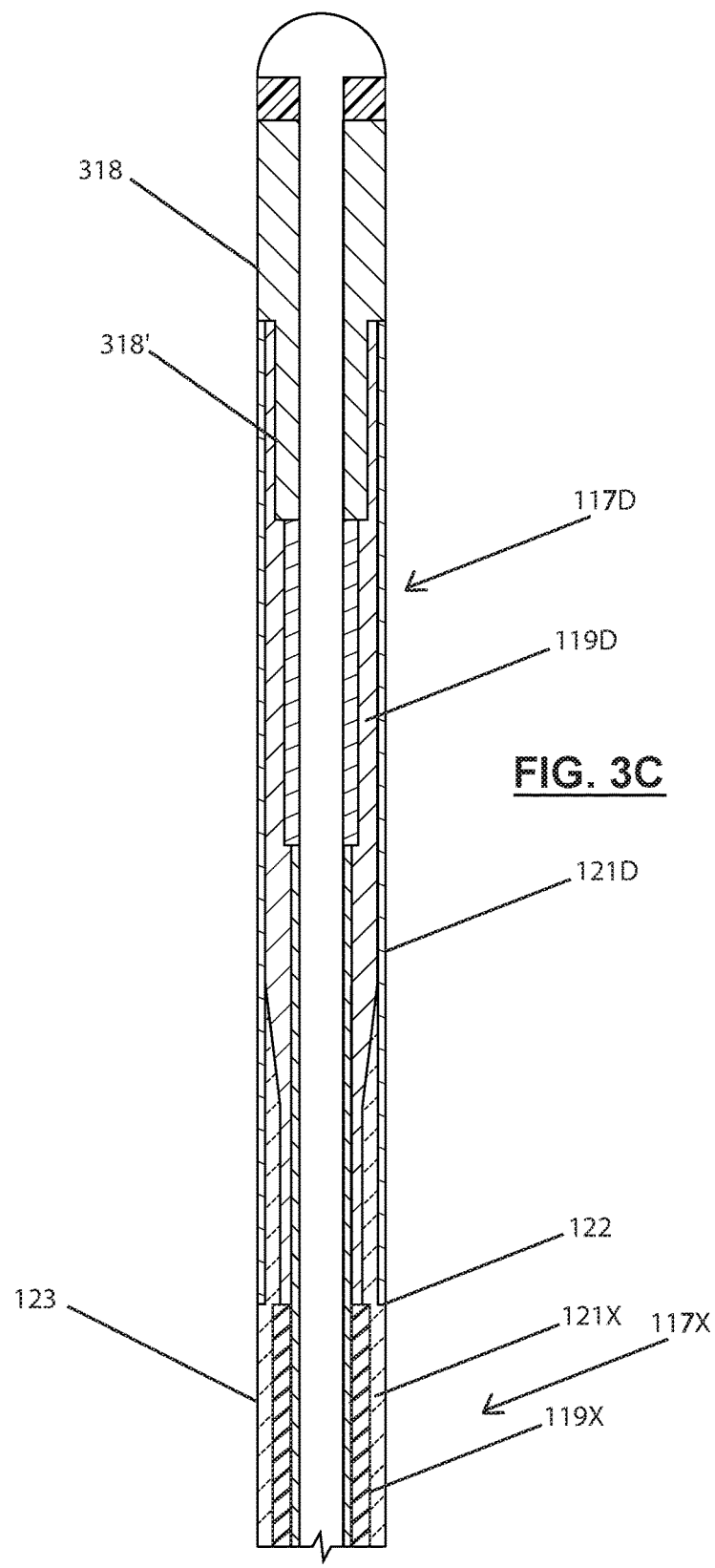

Conversely, in some embodiments, as shown in FIG. 3C, the joint or joint structure is created in such a way that the PTFE layer forming the thermal barrier 121D overlaps or extends over the Pebax layer forming the second outer insulation layer 121X of the intermediate insulation segment 114X with the PTFE layer being on top and extended on top of the Pebax layer. This may help reduce material flaring at the joint, as the PTFE layer that is provided on the outside is stiffer and may be thicker than the Pebax layer and thus may be less susceptible to material flaring. Furthermore, RF guidewire 100F, during use, will be advanced distally into the vasculature in a direction that is parallel to the RF guidewire and as such, to the PTFE layer. Since the advancement of the RF guidewire 100F will be in a distal direction, the forces exerted against the RF guidewire 100F will be directed proximally, which means that less force is exerted in the opposite or distal direction, against the proximal edge 122 of the PTFE layer, which may additionally minimize the risk of material flaring.

As such in some such examples, an overlap exists between one or more layers of the intermediate and distal insulation segments (114X, 114D). More specifically, an overlap exists between the second outer insulation layer 121X and the outer insulation layer or thermal barrier 121D. The second outer insulation layer 121X may be an outer polymer layer which may comprise a substantially flexible outer polymer layer. The thermal barrier 121D for example may also comprising an outer polymer layer. In other words, the area where the distal 114D and intermediate 114X insulation segments meet forms a joint. Specifically the area where the substantially flexible outer polymer layer 121X and the thermal barrier 121D meet forms a joint where the substantially flexible outer polymer layer 121X of the intermediate insulation segment 114X overlaps and is positioned over the thermal barrier 121D of the distal insulation segment.

Example 3D

In another example, as shown in FIG. 3D an adhesion layer is provided (as a first outer insulation layer 119D) underneath a polyimide tube (that functions as a second outer insulation layer or secondary heat shield 121D) to secure the heat resistive layer of polyimide. The adhesion layer 119D may additionally provide better adhesion of the overlapped outer insulation layer 117X (along the intermediate insulation segment 114X) to the heat resistive or insulative tip 117D.

Still alternatively, in some embodiments, the RF guidewire 100F comprises an alternate architecture where in one example, the core wire 202 is substantially thicker than embodiments described herein above, that provides the rigidity and where the electrically insulative inner insulation layer 115R and the inner and outer insulation layers along the proximal, intermediate and distal insulation segments (114P, 114X, 114D) comprise relatively soft polymers.

Still alternatively, in another example, the RF guidewire 100F may comprise an alternate architecture where in one example, a substantially rigid electrically insulative inner insulation layer 115R is provided over the core wire 202, where the one or more outer insulation layers (117P, 117X, 117D) along the proximal, intermediate and distal segments (114P, 114X, 114D) comprise a substantially soft polymer.

Still alternatively, in another example, the RF guidewire 100F may comprise an alternate architecture where in one example, a substantially rigid electrically insulative inner insulation layer 115R is provided over the core wire 202, where the one or more outer insulation layers (117P, 117X, 117D) along the proximal, intermediate and distal segments (114P, 114X, 114D) comprise a substantially rigid polymer. In one example electrically insulative inner insulation layer 115R is polyimide and where one or more outer insulation layers (117P, 117X, 117D) comprises HDPE.

Still alternatively, another other suitable insulation material may be used for any of the insulation layers such as ceramic.

Distal Device Architecture

Referring again to FIG. 1A, the remainder of the device architecture, specifically along the distal portion of the device 100, is described herein below, in accordance with embodiments of the present invention. In one embodiment, as shown in FIG. 1A, the electrosurgical device 100 defines a distal region 104 having a heat shield or heat sink 118 disposed at or near the distal end of the core wire 202 substantially distal to the insulation layer 114. In this embodiment, the heat shield or heat sink 118 is positioned between the insulation layer 114 and the energy delivery component, such as electrode tip 112 positioned at the distal end of core wire 202. The heat shield 118 can also be referred to as an electrically insulative thermal shield.

The heat shield 118 is an electrical and thermal insulator that functions to insulate and thus protect the device proximal region 106, for example the insulation layer 114 located in proximal region 106, from the heat generated at the electrode tip 112 and functions to prevent arcing between the electrode tip and the device proximal region 106. The device proximal region is the portion of the device that is proximal to the heat shield 118. In some embodiments, the heat shield 118 has a thermal conductivity that allows the heat shield 118 to dissipate heat by effectively conducting heat away from the electrode tip 112. This may prevent the heat shield 118 from being damaged due to excessive heat generated at the electrode tip 112.

In one embodiment, the heat shield has a thermal conductivity k, that is greater than about 1 Watt/mK. In other embodiments, the heat shield has a thermal conductivity k that is greater than about 2 Watts/mK. In some embodiments the heat shield 118 may comprise glass or a ceramic such as alumina, aluminum oxide, zirconia toughened alumina (ZTA) or zirconium oxide. In one example, the heat shield 118 comprises a ceramic 218 that is made of pure alumina or sapphire crystal comprising a single/mono crystal aluminum oxide. In other embodiments, other ceramics such as Silicon Nitride or Silicon Carbide may be used. In still other embodiments, any other suitable ceramic may be used as heat shield 218. In still other embodiments, the heat shield 118 may comprise any other suitable insulative material that is not damaged by the temperatures generated at electrode tip 112. Additionally, in some embodiments, the heat shield 118 has sufficient mechanical strength which may allow it to be machined into the desired shape such as a tubular cylindrical shape.

In one embodiment, the electrode tip 112 is a mono-polar active electrode. When arcing is initiated at the mono-polar active electrode, high temperatures are created at the electrode tip 112 and within the region of tissue surrounding the electrode tip 112. The ceramic heatshield 218 is thermally insulative and withstands the high temperatures generated while maintaining good dielectric properties. In other words, ceramic heat shield 218 additionally functions as an electrical insulator. In some embodiments, the thermal conductivity of ceramic heat shield 218 is sufficient to allow heat to be dissipated away from the active electrode tip 112 while minimizing transmission of heat to the device proximal region 106 having the insulation layer 114. Thus, a proximal segment of the electrosurgical device 100 is effectively shielded from arcing at the electrode tip 112 as well as from the heat generated at the electrode tip 112. In other words, the ceramic heat shield 218 prevents degradation of the insulation layer 114 as may occur due to its proximity to arcing. Thus, the heat shield 118 acts as a protective barrier between active electrode tip 112 and the insulation layer 114 by electrically insulating the electrode tip 112 from arcing at the electrode tip 112 and by providing thermal protection for the insulation layer 114 by substantially thermally insulating the device proximal region 106 from the electrode tip 112. In other words, in some embodiments, a single thermal shield 118 functions as a barrier between the device proximal region 106 and the electrode tip 112 and provides provide both the benefit of preventing arcing between the device proximal region 106 and the electrode tip 112 as well as protecting the device proximal region from the heat produced by the delivery of energy through the electrode tip 112. In one embodiment, the heat shield 118 functions to electrically and thermally isolate the device proximal region 106 including the insulation layer 114 from the device distal tip 108 including the electrode tip 112.

In one example, the heat shield 118 is a ceramic comprising a tubular single crystal aluminum oxide (sapphire) cylinder 218 that is a thermal insulator having suitable thermal conductivity and mechanical strength. The sapphire ceramic heat shield 218 can support voltages used to initiate arcing and can withstand higher temperatures resulting from arcing at the distal tip 108. Furthermore, the single crystal Aluminum Oxide ceramic (sapphire) heat shield 218 also provides mechanical strength and helps impart rigidity to the distal region 104 of the electrosurgical device. This may help reduce the risk of the heat shield 218 from cracking when the device 100 is pushed or manipulated during the manufacturing process. Thus ceramic heat shield 218 may both provide thermal insulation as well as mechanical strength and/or rigidity. In one specific example, the ceramic heat shield 218 is a single crystal Aluminum oxide heat shield 218 that is a tubular cylinder having a longitudinal length of about 2-3 mm, for example about 2.54 mm. In some such embodiments, the tubular cylindrical ceramic has an inner diameter of about 0.2 to about 0.4 mm, for example about 0.292 mm and an outer diameter of about 0.5 to about 0.8 mm, for example about 0.660 mm. In one embodiment, the heat shield 118 comprises material that can be viewed using an imaging modality. In one such example, the heat shield 118 is radiopaque.

As described above, device 100 may include one or more radiopaque bands 130. The placement of the radiopaque bands 130 onto to the inner core 202 may also help increase rigidity of the device 100. In one embodiment, the combination of the radiopaque bands 130, the core wire 202 and the heat shield 218, provides sufficient rigidity to enhance pushability of device 100 through tissue, for e.g. an occlusion. In one embodiment, a radiopaque band 130 is positioned proximal to the heat shield 118. In one example, the radiopaque band 130 is secured to the core wire 202 to retain/support the heat shield 118 in position. In another example, the heat shield 118 is retained or supported in place by the core wire 202. In such an embodiment, the core wire 202 has a wider section adjacent and proximal to the distal section as shown in FIG. 7B. The heat shield 118 is loaded onto the distal section and retained by this wider section of the core wire 202.

In one embodiment, as shown in FIG. 1B, multiple radiopaque bands 130 are positioned on the core wire 202. These provide reference markings which when viewed under fluoroscopic imaging provide guidance to the physician for positioning the device 100 within a patient's body and/or for advancement of the device 100 during use. The radiopaque bands 130 may comprise materials such as platinum, iridium, gold, silver, tantalum and tungsten or their alloys, or radiopaque polymer compounds. In one specific example, as mentioned above, platinum is used for the radiopaque bands 130.

As illustrated in FIG. 1A, the electrode tip 112 forms the energy delivery component of electrosurgical device 100, via which energy is delivered. As shown, the active electrode tip 112 is positioned distal to the heat sink 118 at the distal tip 108. The distal tip 108 defines the part of the distal region 104 that is distal to the heat sink. A junction 122 is formed forms between the insulation layer 114 and the heat sink 118.

In some embodiments, a seamless transition is provided at the junction 122 between the insulation layer 114 and the ceramic 218. In one embodiment, the insulation layer 114 extends over the heat-shield at the junction 122 as shown in FIG. 1A. Therefore, an overlap of insulation layer 114 forms over the heat-shield 218 forming a sealed junction. In one specific example, the insulation layer overlaps the proximal portion of the heat-shield 218 by about 0.5 mm to about 2 mm, for example about 1 mm. The overlap of the insulation layer 114 at junction 122 with the ceramic heat shield 218 helps to limit the arcing to the electrode tip 112 at the distal tip 108. This may help minimize arcing observed behind the heat shield near the junction 122 and may help minimize degradation of the insulation layer 114 from the heat generated at the electrode tip 112 from the delivery of electrical energy through the electrode tip 112.

Figure 4A:
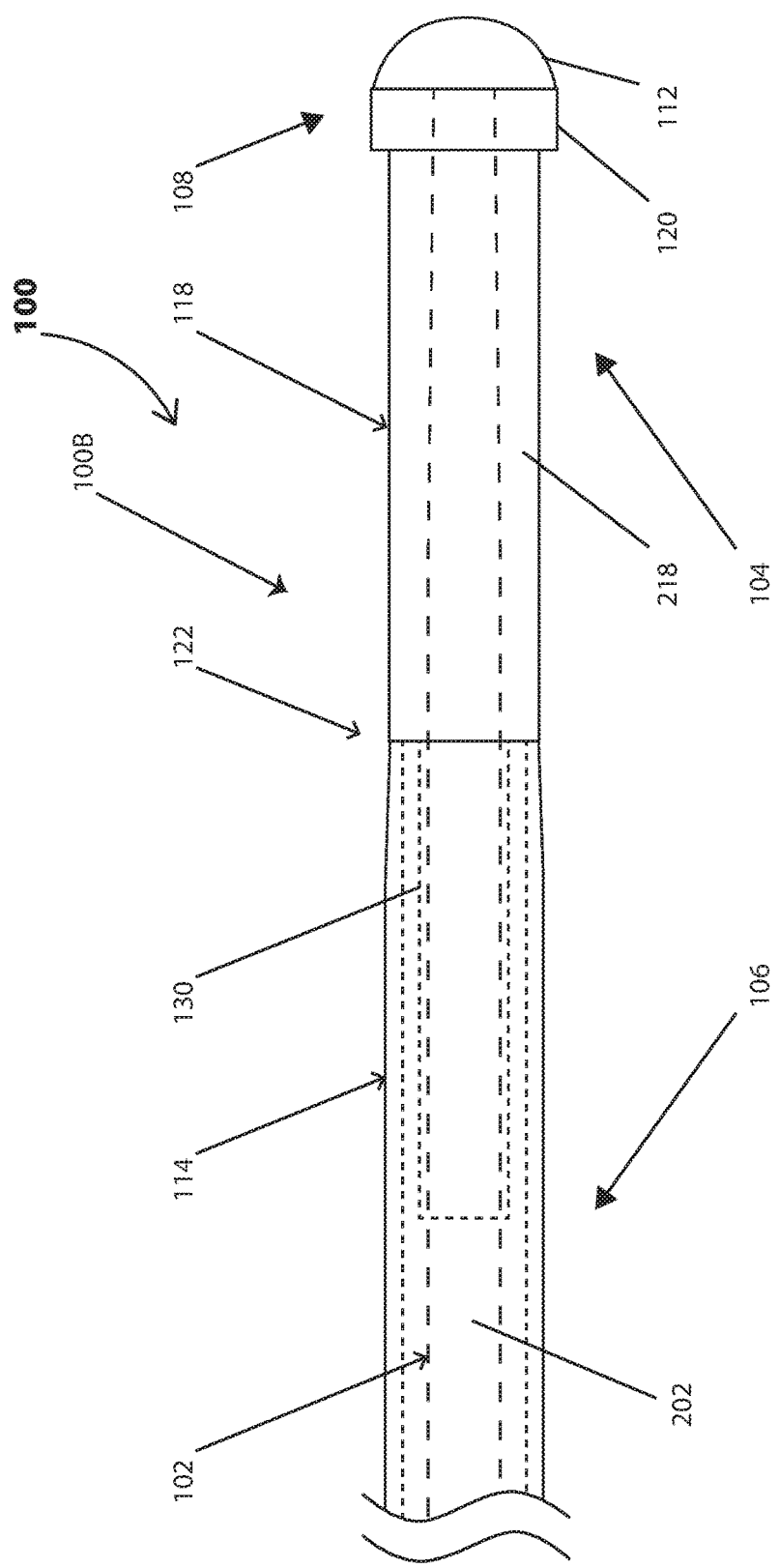
FIG. 4A is an illustration of an electrosurgical device in accordance with an alternate embodiment of the present invention.
Figure 4B:
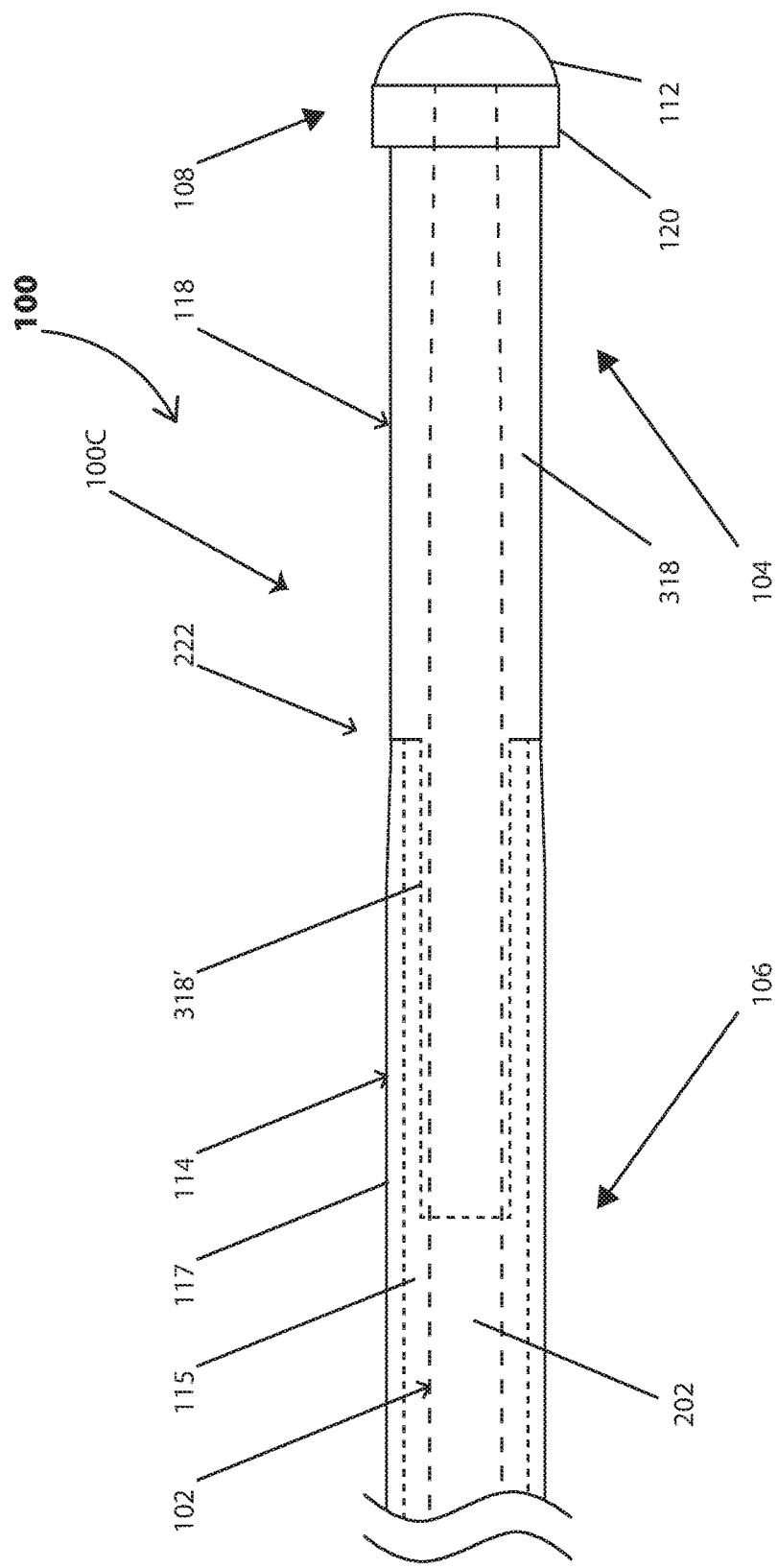
FIG. 4B is an illustration of an electrosurgical device in accordance with an alternate embodiment of the present invention.

In another embodiment, the insulation layer 114 and the heat shield 118 such as ceramic heat shield 218 may be flush against one another (or in other words may abut one another) to form a junction therebetween as shown by device 100B in FIG. 4A. In still another embodiment, a step-down heat shield 318 may be used as shown by device 100C in FIG. 4B. The heat shield 318 may be a ceramic heat shield having properties similar to those mentioned previously for ceramic heat shield 218 and/or or heat shield 118. In some embodiments, the heat shield 318, for e.g. a tubular ceramic heat shield, is wider at its distal portion than at its proximal portion. This allows the insulation layer 114 to form around the proximal portion of the heat-shield 318. The insulation layer 114 is formed flush against and surrounding the proximal portion of the heat shield 318. This allows for a smooth transition between the heat shield 318 and the insulation layer 114, and may also allow for a secure junction 222 to be formed between the two materials. This helps ensure that the wire 202 is not exposed at the junction 222. This also helps minimize any shoulder effect (also known as 'hot spots') which may otherwise be created between the insulation layer 114 and the heat shield 318. Thus, the risk of a discontinuity forming due to exposure of wire 202 at the junction 222 is minimized. This allows arcing to be limited the electrode tip 112. Furthermore, the smoother outer profile at the junction 222 may prevent tissue from getting caught and snagging at the junction 222 which may allow device 100 to traverse through the occlusion relatively easily.

In one embodiment of the present invention, energy is supplied from the energy source through the elongate member 102 to the energy delivery component comprising electrode tip 112. The electrode tip 112 is coupled to the elongate member distal end which receives energy from the energy source. The electrode tip 112 is configured and sized such that a sufficiently high current density is provided at the electrode tip 112 to generate arcing in a region of tissue when the electrode tip 112 is positioned proximate the region of tissue. This allows a channel to be created through at least a portion of the region of tissue. In one specific example, the electrode tip 112 has an outer diameter (OD) of between about 0.027" to about 0.032" and a longitudinal length of between about 0.15 mm to about 0.20 mm.

In some embodiments, the electrode tip 112 may be attached to the elongate member distal end. In other embodiments, laser welding is used to form electrode tip 112 at the distal end of the elongate member. In still other embodiments, other methods may be used to provide the electrode tip 112. In some embodiments the electrode tip 112 defines the electrode. In other words, the electrode tip 112 forms the energy delivery component of electrosurgical device 100. In one embodiment, the electrode tip 112 comprises a segment of a sphere, i.e. it is substantially spherical in shape. For example, substantially the entire energy delivery portion comprising the electrode tip 112 (i.e. the entire surface from which energy is delivered) forms a segment of a sphere. For example, the electrode tip 112 is a hemispherical or a rounded electrode tip 112 as shown in FIGS. 1-4C, 8 and 9A. The shape and surface area of the electrode tip 112 allow the current density, and thus arcing, to be focused/concentrated at the distal most tip. Put differently, the electrode tip 112 comprises a dome shaped electrode tip 112 which allows for increased current density at the distal most tip, which facilitates the initiation of arcing and thereby allows the electrosurgical device 100 to create a channel through tissue.

As described above, and as shown in FIG. 9A, the electrode tips 112a and 112a' are shaped substantially as a segment of a sphere. In an alternate embodiment, the electrode tip 112b may comprise a "mushroom shaped" tip as shown in FIG. 9B. Furthermore, in some embodiments, the tip 112 is substantially atraumatic, for e.g. as shown by electrode tips 112a and 112a'. In another embodiment, the electrode tip 112c may comprise a bi-arcuate tip, as shown in FIG. 9C. A laser weld process may be used that allows a cavity or bowl to be formed at the center of the electrode tip 112c which may allow electrical energy and thus increased current density to be concentrated within the cavity. Thus arcing may be concentrated at the central region of the electrode tip 112c.

In some embodiments, a support structure 120 may be positioned adjacent the elongate member 102 distal end, distal to the heat shield 118 and laser welding may be used to form electrode tip 112c onto the support structure. Similarly, in some of the other embodiments shown in FIGS. 9A-9D, the electrode tip 112 may be formed by laser-welding the distal end of the core wire 202 onto a support structure 120 positioned distal to the heat shield 118.

In a further embodiment, the electrode tip 112d forms a conical shape and tapers towards its distal end as shown in FIG. 9D. This may allow arcing to be concentrated at the distal most end of the electrode tip 112d having a lower surface area and thus a higher current density. In one example, as shown in FIG. 9D, the distal most end of the conical electrode tip 112d may be rounded in shape. This may allow the electrode tip 112 to be substantially atraumatic when inserted for example, into the body vasculature. In an alternate embodiment, an electrode tip 112e may comprise a ball shaped electrode, as shown in FIG. 9E. In some embodiments, the electrode tip 112 may have a•surface geometry that allows sufficient current density to accumulate the electrode tip 112 that is sufficient to generate arcing to enable the electrosurgical device 100 to traverse through a tissue such as an occlusion. In some embodiments, the electrode tip 112 may be formed integrally with the elongate member 102. In other embodiments the electrode tip 112 may be otherwise attached to the elongate member 102 to form a secure connection therewith.

In some embodiments the electrode tip 112 is positioned distal to the heat shield 118. In some embodiments, the electrode tip 112 may be positioned substantially adjacent to the heat shield 118. In one example, the electrode tip 112 may be positioned distal to and adjacent to the distal face of the heat shield 118 as shown in FIGS. 9A-9D. In one example, the heat shield 118 extends substantially radially along a proximal face of the electrode tip 112. In one example, a platinum band may be positioned proximal to the heat shield 118. In another embodiment, the electrode tip 112 is positioned distal to and adjacent a support structure 120 that comprises an annular tubular structure through which core wire 202 is threaded as shown in FIGS. 1A, 1B and 4A-4C. In some embodiments, the electrode tip 112 may have an outer diameter that is equal or greater than the diameter of the distal components which are adjacent the electrode tip 112, such as the heat shield 118 or a combination of the heat shield 118 and the support structure 120. In other embodiments, the electrode tip 112 and additionally the support structure 120 both have an outer diameter which is equal to or greater than diameter of the heat shield 118. In such embodiments, when the electrode tip 112 is used to create a channel portion through tissue for e.g. an occlusion, by delivering energy through the electrode tip 112, a channel portion is created that is at least as wide as the electrode tip 112 outer diameter. This allows at least the electrosurgical device distal region 104 to be advanced through the occlusion. In still other embodiments, the electrode tip 112 may have a diameter that is less than that of the heat shield and/or the support structure. In some embodiments the electrode tip 112 helps retain the heat shield 118 in position within the device 100. In other words, the electrode tip 112 helps secure the heat shield 118 in place.

In some embodiments, as mentioned above, a support structure 120 is provided distal to the heat shield 118. The support structure 120 provides a distal surface on which the electrode tip 112 may be positioned and/or formed, for example using a welding process. In one specific example, a laser welding process is used and the support structure 120 provides a substantially planar distal face onto which the dome-shaped electrode tip 112 is formed. In one instance of this example, the support structure 120 comprises a material that can withstand the laser welding process and can bond well with the core wire 202. The welding process allows the electrode tip 112 to fuse with the support structure 120 at the interface between the two. Additionally, in some embodiments, the support structure 120 has sufficient mechanical strength to allow it to be machined. Both the core wire 202 and the support structure 120 may be formed from biocompatible materials. In one specific example, the support structure 120 comprises a metal such as Tantalum and the core wire 202 comprises Nitinol. When the Nitinol core wire 202 is laser welded it fuses with the Tantalum support structure 120 at the interface between the two materials. An integral bond is formed at the boundary between the Nitinol electrode tip 112 and the tantalum support structure 120. The Tantalum support structure 120 allows the dome of the Nitinol electrode tip 112 to be formed on a flat surface. In other words, the Tantalum support structure 120 functions as a base to allow the Nitinol electrode tip 112 to be formed onto it.

In some embodiments, the support structure 120 may comprise materials such as tantalum, iridium, gold or stainless steel. In other embodiments, any other suitable material may be used. In one example, the support structure 120 is radiopaque and provides the physician with a visual indication of the location of the electrode tip 112 under imaging.

This helps determine the location of electrode tip 112 within the patient's body during use. In one specific example, an annular tubular structure comprising radiopaque tantalum metal is used as the support structure 120. The support structure 120 is threaded onto the distal end of the core wire 202 and the electrode tip 112 is positioned or formed distal to and adjacent to the support structure 120, the support structure 120 being positioned distal to heat shield 118. In some embodiments, the tantalum support structure 120 has an inner diameter of about 0.2 mm to about 0.3 mm, for example about 0.279 mm, an outer diameter of about 0.8 mm to about 0.9 mm, for example about 0.812 mm, and a longitudinal length of about 0.2 mm to about 0.3 mm, for example about 0.254 mm.

In some embodiments, the support structure 120 is electrically conductive and forms a part of the electrode. Thus, the support structure 120 together with the electrode tip 112 can be understood to form the energy delivery component. In one such example, a Nitinol electrode tip 112 is formed on a tantalum support structure 120 that is positioned distal to the heat shield 118. The electrode tip 112 is shaped to provide current density sufficient to generate arcing to create a channel through a region of tissue. Additionally, arcing may be generated at the tantalum support structure 120, for example on its sides or radial edges and at the edges/corners of the support structure 120 at a discontinuity. In some examples, the heat shield 118 is flush with the support structure 120. In other embodiments, the heat shield may not be positioned such that it is flush with the support structure 120 and there may be arcing at the junction/boundary between support structure 120 and the heat shield 118. In other words, if there is a gap at the proximal boundary of the support structure 120, there may be some arcing generated there. In one example, a ceramic filler may be used at this junction to fill the gap. In some applications/uses, for example if there is coagulum formation at the electrode tip 112, then arcing may be generated at the support structure 120. In another example, a substantially thin support structure 120 is used whereby arcing may be generated at the support structure 120. In some embodiments, the arcing observed at the support structure 120, in addition to arcing at the electrode tip 112, may help device 100 to traverse through a relatively large occlusion.

In alternate embodiments the support structure 120 may not be electrically conductive. In some embodiments, the support structure 120 may be flush with and positioned adjacent the electrode tip 112. In some embodiments the support structure 120 and the electrode tip may be attached or secured to one another. In other embodiments, the support structure 120 and the electrode tip 112 may not be attached. As mentioned, in one example, the support structure 120 is electrically conductive and forms an electrode together with electrode tip 112. In another example, the electrode tip 112 substantially forms the electrode. Thus, the electrode tip 112 or the support structure 120 in conjunction with electrode 112 define the energy delivery component of electrosurgical device 100 through which energy can be delivered, for example to a region of tissue within a patient's body.

Various methods may be used to provide an electrode tip 112 that is shaped substantially like a segment of sphere. This may include an electrode tip 112 that is rounded or hemispherical in shape. In some embodiments, the electrode tip 112 that is shaped like a segment of a sphere may be removably attached to the distal end of the electrosurgical device 100. For example, the electrode tip 112 may be a rounded cap electrode and may be removably affixed to the core wire 202 and/or to the support structure 120. Alternatively, in some embodiments, an electrode tip 112 may be coupled/attached directly to a distal end of the elongate member 102 distal to and adjacent to the heat shield 118. As mentioned above, in other embodiments the electrode tip 112 may have surface geometries similar to those shown in FIGS. 9A-9D. In one embodiment, a friction fit may be used such that the electrode tip 112 co-operatively engages with either the elongate member 102 and/or the heat-shield 118. In some embodiments, the electrode tip 112 may be mechanically secured to the elongate member 102 and may abut the heat shield 118 such that it rests against the heat shield 118. In one specific example, the elongate member 102 may comprise a Nitinol wire and the electrode tip 112 may comprise a rounded Nitinol cap and may be attached to the distal tip of wire 102. Alternatively, the electrode tip 112 may comprise a Nitinol 'ball' or sphere. A hole may be created/ground in the ball and the elongate member 102 such as the core wire 202 may be received within the hole and attached thereto. In some embodiments, the electrode tip 112 may be may be secured to the elongate member 102 and/or heat shield 118 by an adhesive. In one example, the adhesive may comprise an epoxy. In one embodiment, the electrode tip 112 may be attached to wire 102 using a melt-processing method. In some embodiments, the heat shield 118 extends substantially radially along a proximal face of the electrode tip 112. In alternate embodiments, the heat shield 118 extends substantially radially along a proximal face of an annular structure such as support structure 120. In one specific example, the support structure 120 is an annular structure which is electrically conductive and forms a part of the electrode as described hereinabove.

Figure 4C:
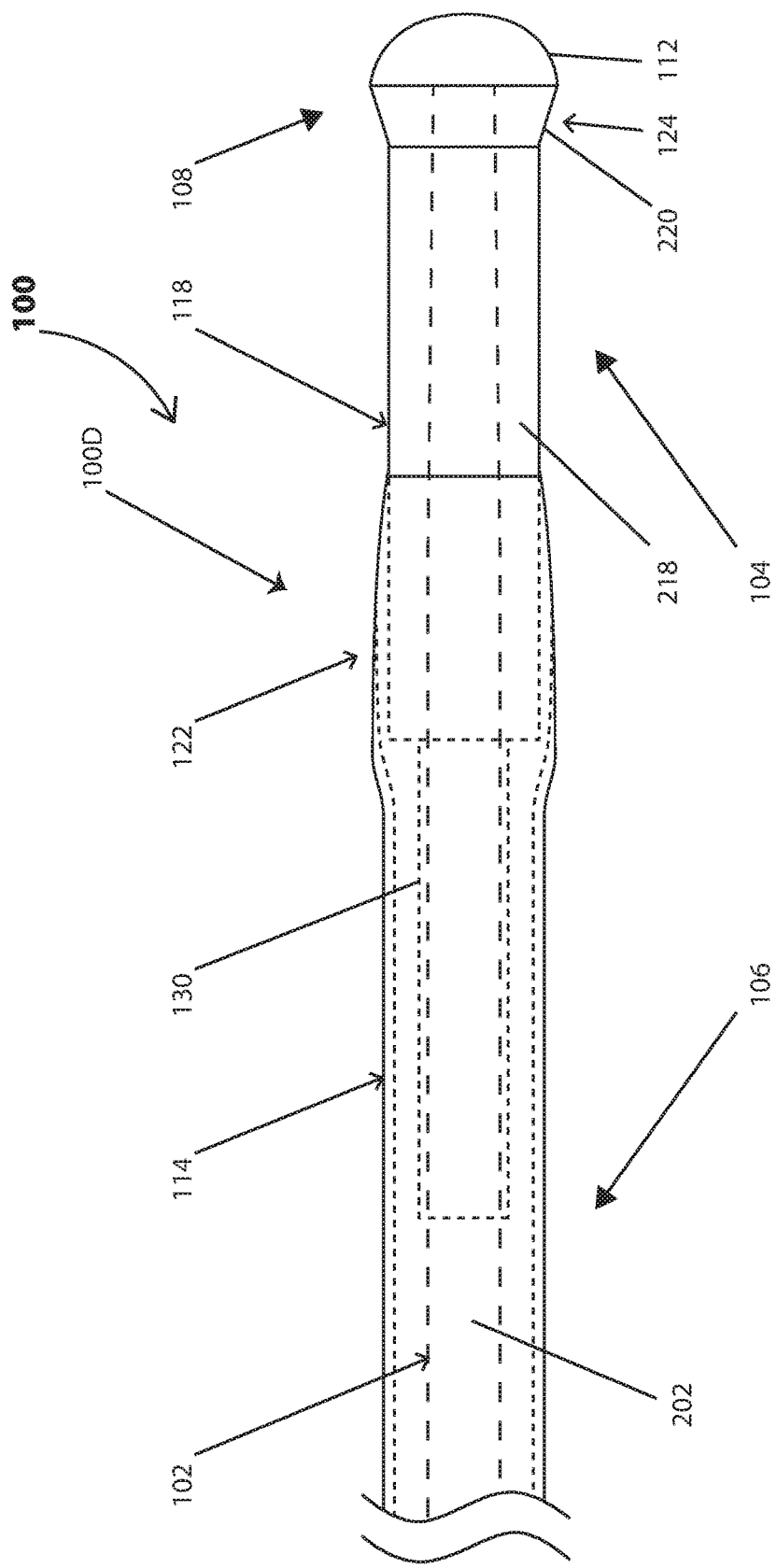
FIG. 4C is an illustration of an electrosurgical device in accordance with an alternate embodiment of the present invention.

In one embodiment of the present invention, a support structure 220 comprises a tapered profile 124, for example as shown in FIG. 4C. The support structure 220 may have the properties as discussed above for support structure 120. In one example, the support structure 220 comprises an annular structure that has an outer diameter that gradually tapers from its distal end towards its proximal end as shown in FIG. 4C. In one embodiment, the tapered support structure 220 has a distal outer diameter (OD) that matches the outer diameter of the distal electrode tip 112. Furthermore, the tapered support structure 220 has a proximal outer diameter (OD) that matches the outer diameter of the heat shield 118. Thus, a smooth outer profile is created by the tapered support structure 220 which facilitates the advancement of device 100D within tissue within a patient's body. The tapered profile 124 minimizes the risk of tissue snagging or catching at the proximal boundary of the support structure 220. This minimizes the risk of charred tissue getting caught proximal to the electrode tip 112 and the support structure 220. This may further facilitate forward advancement of the device 100D as tissue is targeted by the active electrode tip 112 at the distal tip 108. The tapered profile 124 may also facilitate backward movement or retraction of device 100D during use, for example, within a patient's body (for e.g. within a vessel lumen). In one example, the tapered support structure 220 comprises tantalum. Thus, the tapered profile of tantalum having a distal outer diameter (OD) larger than its proximal OD may allow easier traversal through the occlusion. The distal OD of tantalum may be greater than the device 100D OD along a portion of the device 100D proximal to the support structure.

In some embodiments of the present invention, the electrosurgical device 100 may have an outer diameter (OD) at the distal tip 108 which is greater than the outer diameter (OD) along a portion of the device 100 proximal to the distal tip 108, such as OD of heat shield 118. The wider OD at the distal tip 108 may help facilitate traversal of the electrosurgical device 100 through tissue such as an occlusion. In one example, during use, the larger distal tip OD of device 100 can create a puncture in tissue that is greater than the device OD proximal to the distal tip 108. In other words, the larger distal tip OD allows a channel to be created through tissue, for example an occlusion that is wider than a segment of device 100 proximal to the distal tip 108. Thus, the wider OD at the distal tip allows the device 100 to traverse easily through the occlusion with minimal risk of hindrance in the device path. This may allow the device 100 to cross with ease through the channel created. The larger distal OD also minimizes the risk of tissue being caught at the junction 122, for e.g. at the over-lap of the insulation layer 114 with the heat shield 118. Furthermore, a portion of the device proximal region 106 may have an outer diameter (OD) that is greater than the distal tip OD. This may allow the device 100 to further dilate the occlusion. In one example, the proximal portion of the device proximal region 106 has an OD that is wider than the distal tip OD. Additionally, in one example, the device proximal region 106 has a tapering profile that increases in diameter towards its proximal portion.

In accordance with an embodiment of the present invention, electrosurgical device 100 allows traversal through occlusions, which may include occlusion harder portions, and occlusion softer portions. In some embodiments, the electrosurgical device 100 provides a dome-shaped electrode tip 112 which provides sufficiently intense arcing to facilitate crossing of the device 100 through at least a portion of the harder part of the occlusion.

Figure 8:
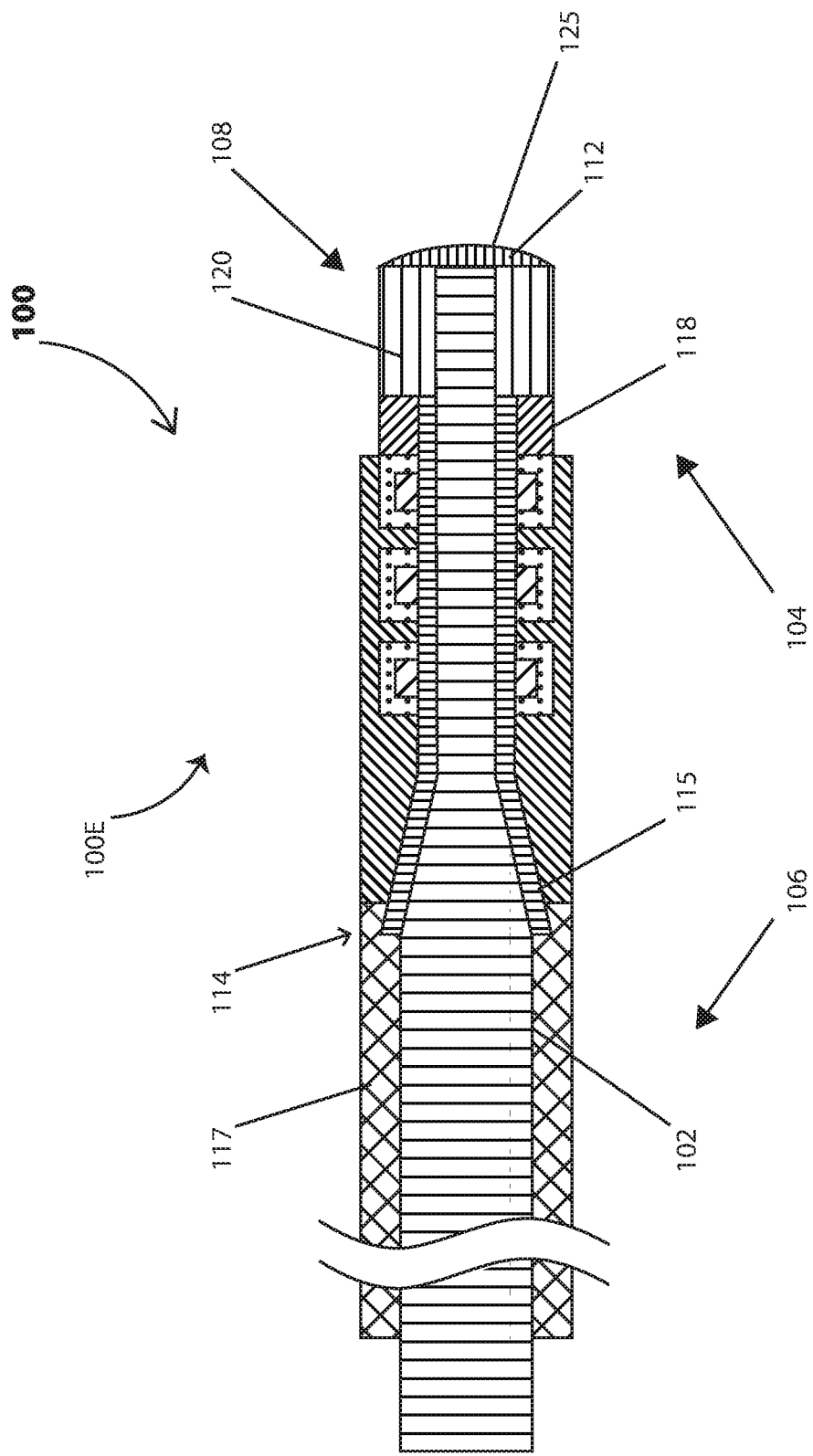
FIG. 8, in a partial side cross-sectional view, illustrates an embodiment of an energy delivery apparatus.

Referring to FIG. 8, the energy delivery apparatus, such as electrosurgical device 100E includes an elongate member, such as a substantially elongated electrical conductor 102, which may be any suitable conductor, such as a wire or a cable made out of a suitable electrically conducting material, such as for example. Nitinol, stainless steel, gold, platinum, titanium. Silver, or alloys thereof. The electrical conductor 102 is substantially elongated and defines a conductor proximal end and a substantially longitudinally opposed conductor distal end. An electrode tip 112 is electrically coupled to the electrical conductor 102 and located at a predetermined location there along, for example adjacent to conductor distal end. The electrode tip 112 is provided for delivering electrical energy at a target location.

A proximal region 106 of the electrosurgical device such as a proximal region the electrical conductor 102 having an electrically insulating layer disposed thereon, is positioned in a substantially spaced apart relationship relative to the electrode tip 112.

Spacing apart the proximal region 106 of the electrosurgical device 100 from the electrode tip 112 ensures that any temperature increase caused by the delivery of electrical energy to the target location only minimally affects the device proximal region 106.

In the embodiment of the invention shown in FIG. 8, the proximal region 106 of the electrosurgical device is substantially longitudinally spaced apart from the electrode tip 112. More specifically, the electrode tip 112 is located distally relatively to the device proximal region 106. For example, the electrode tip 112 is located substantially adjacent to the conductor distal end. It is within the scope of the invention to have an electrode tip 112 that is formed integrally by a section of the outermost surface of the electrical conductor 102.

In this embodiment, the electrode tip 112 defines tip distal surface 125 that is shaped substantially similarly to a portion of a sphere, i.e. rounded. This helps to ensure that injuries that may be caused to the body vessels, through movements of the electrode tip 112 through these vessels, are minimized.

In some embodiments of the invention, the energy delivery apparatus 100E includes an electrically insulating material substantially covering the electrical conductor 102, such as for example and non-limitingly, Teflons®, such as polytetrafluoroethylene (PTFE), fluorinated ethylene propylene copolymer (FEP), perfluoroalkoxy (PFA), or ethylene and tetrafluoroethylene copolymer (ETFE, for example Tefzel®), or coatings other than Teflons®, such as polyetheretherketone plastics (PEEK™), parylene, certain ceramics, or polyethylene terpthalate (PET}. In some embodiments, the electrically insulating material forms a layer that extends substantially radially outwardly from the electrical conductor 102. The electrically insulating material is described in further details hereinbelow.

In some embodiments of the invention, the energy delivery apparatus 100E further includes a heat shield 118 made out of a substantially thermally insulating material, for example, and non-limitingly, polytetrafluoroethylene (PTFE), which has a thermal conductivity of about 0.3 W/m-K. In this embodiment the heat shield 118 may have a thickness of at least about 0.025 mm. In other embodiments, the thickness of the heat shield 118 may vary, depending on the thermal conductivity of the material being used. The heat shield 118 is located, at least in part, between the electrode tip 112 and the device proximal region 106. The heat shield 118 is provided for further thermally insulating the device proximal region 106 (having an elongate member 102 with an electrically insulating layer disposed thereon) from the electrode tip 112 and from heat produced by the delivery of electrical energy through the electrode tip 112.

In some embodiments of the invention, the heat shield 118 includes o polytetrafluoroethylene (PTFE). The use of PTFE is advantageous as, in addition to having suitable thermal insulation properties, PTFE is also an electrically insulating material (having a dielectric strength of about 24 kV/mm) and, therefore, contributes to the prevention of arcing between the electrode and any metallic material that may be present in the device proximal region 106. In alternate embodiments, other materials, such as for example, Zirconium Oxide, may be used for heat shield 118.

In one embodiment of the invention, the heat shield 118 extends substantially longitudinally from and contacts both the device proximal region 106 and the electrode tip 112. In other words, the heat shield 118 substantially fills a gap between the electrode tip 112 and the device proximal region 106. However, in alternative embodiments of the invention, the heat shield 118 extends substantially longitudinally only from one of the device proximal region 106 and the electrode tip 112 or, alternatively, the heat shield 118 does not contact either one of the device proximal region 106 and the electrode tip 112.

As shown in the drawings, the heat shield 118 is substantially annular and extends substantially radially outwardly away from the electrically insulating material covering the electrical conductor 102. In a very specific embodiment of the invention, the heat shield 118 is substantially annular and has a substantially similar outer diameter as device proximal region 106 and the electrode tip 112. This configuration results in an energy delivery apparatus 100E for which a distal region thereof has a substantially uniform outer diameter, which therefore facilitates navigation of the energy delivery apparatus 100E through body vessels and the creation of channels through occlusions and other biological tissues inside the patient. However, in alternative embodiments of the invention, the heat shield 118, the electrode tip 112 and the device proximal region 106 may all have any other suitable diameters.

In alternative embodiments of the invention, the electrical conductor or elongate member 102 is made more flexible substantially adjacent the conductor distal end than substantially adjacent the conductor proximal end in any other suitable manner such as, for example, by using different materials for manufacturing the conductor proximal and distal regions. It has been found that a suitable material for manufacturing the electrical conductor 102 is Nitinol. Indeed, Nitinol shows super-elastic properties and is therefore particularly suitable for applying relatively large deformations thereto in order to guide the energy delivery apparatus 100E through relatively tortuous paths. Also, since the energy delivery apparatus 100E typically creates channels inside biological tissues through radio frequency perforations, in some embodiments of the invention, the energy delivery apparatus 100E typically does not need to be very rigid.

In some embodiments of the invention, the electrically insulating material or insulation layer 114 is divided into a first electrically insulating material or insulation layer 117 and a second electrically insulating material or insulation layer 115. A first electrically insulating layer 117 made out of the first electrically insulating material substantially covers a first section of the electrical conductor 102. A second electrically insulating layer 115 made out of the second electrically insulating material substantially covers a second section of the electrical conductor 102. The second section is located distally relatively to the first section. Furthermore, the first and second electrically insulating materials may comprise different materials with differing physical properties. For example, in some embodiments, the second electrically insulating material comprises polyimide, while the first electrically insulating material comprises PTFE. This allows for the second electrically insulating layer 115 to be substantially thinner than the first electrically insulating layer 117, while being sufficiently insulative so as to prevent undesired leakage of current. This substantially increases the flexibility of the energy delivery apparatus 100 substantially adjacent the apparatus distal end portion such as distal tip 108. In addition, this provides a material that is substantially more lubricious over the wider section of the energy delivery apparatus 100E so as to facilitate movement of the energy delivery apparatus 100E through body vessels and through channels created within the body.

Applications

An embodiment of a treatment method of the present invention may be useful, for example, to penetrate through a material at least partly occluding a vessel of a body of a patient (such as a stenosis) in order to recannalize the vessel. In such an example, the material to be penetrated may comprise a vascular occlusion having regions of various degrees of toughness and calcification. Thus, this particular application may benefit from utilizing electrical energy in conjunction with the mechanical application of pressure in order to penetrate and traverse the occlusion.

Figure 5:
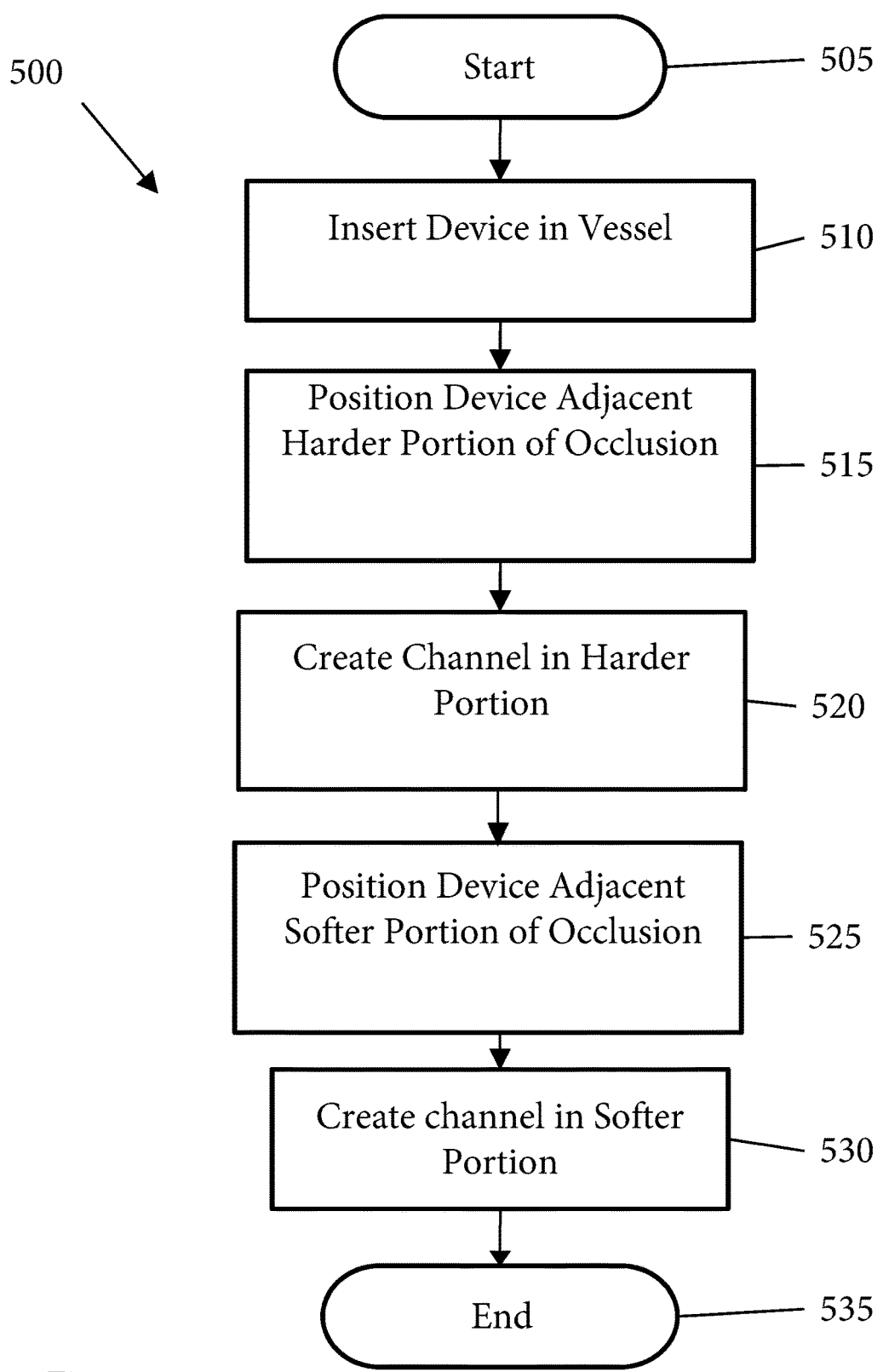
FIG. 5, in a flow chart, illustrates a method for creating a channel in accordance with an embodiment of the present invention.
Figure 6:
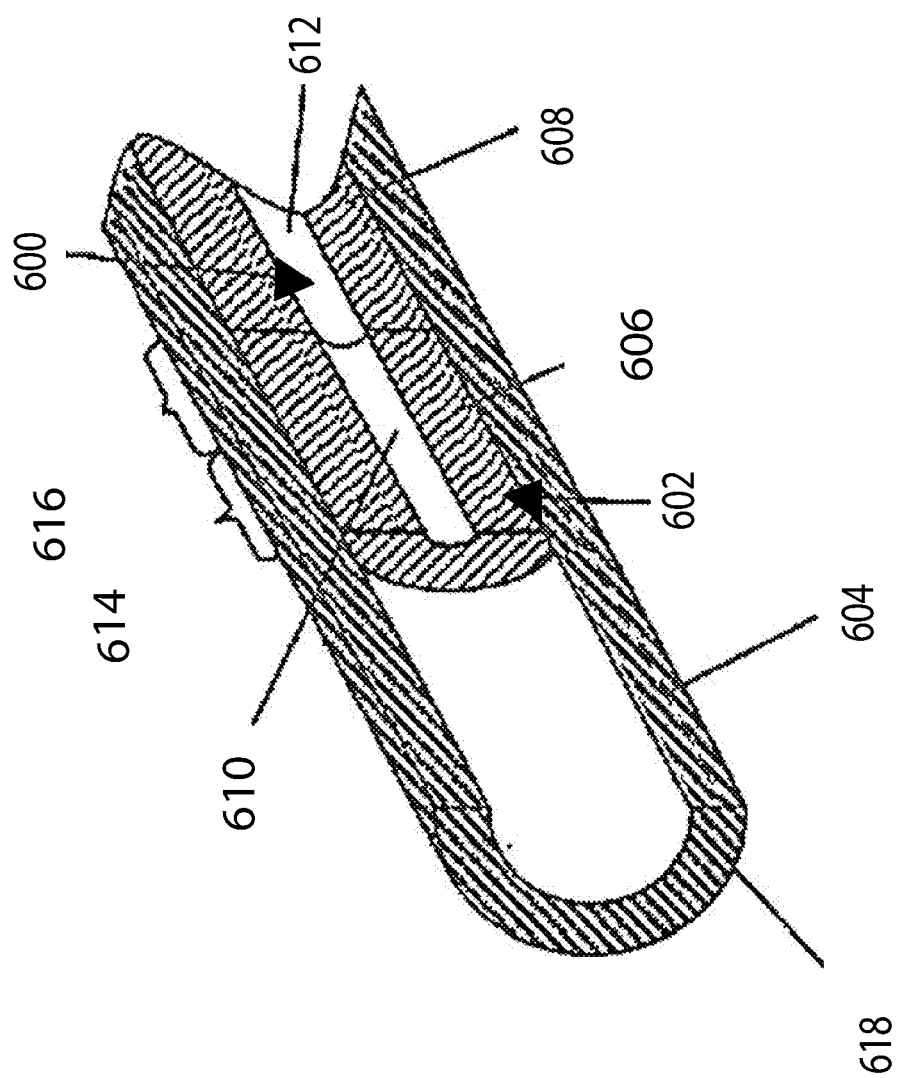
FIG. 6, in a perspective view, illustrates the channel created in an occlusion of a body vessel using the method illustrated in FIG. 5.

R referring to FIGS. 5 and 6, in a more specific example of implementation, the present invention is embodied in a method 500 for creating a channel 600 through an occlusion 602 located in a substantially elongated body vessel 604 of a patient, the occlusion 602 including an occlusion harder portion 606 extending substantially longitudinally relative to the body vessel 602 and an occlusion softer portion 608 extending substantially longitudinally relative to the body vessel 602, the occlusion softer portion 608 being located substantially adjacent to and substantially coaxially with the occlusion harder portion 606. Also, it should be noted that for the purposed of this example and of the appended claims, the term body vessel applied to any suitable body structure defining a lumen, such as for example a blood vessel, a bile duct, an airway, and various tubes and/or ducts associated with the digestive system, the urinary tract and/or the reproductive system, among other possibilities.

For example, it has been found that the proposed method is well suited to the creation of channels through plaque partially or totally occluding a blood vessel. Such occlusions often have harder portions, for example end caps thereof, and located substantially adjacent softer portions, for example the portion of the occlusion located between the end caps.

Also, the person skilled in the art will readily appreciate that the channel 600 is not necessarily a self-supporting channel 600. Therefore, in some embodiments of the invention, the channel 600 is further dilated or receives a stent, or is both dilated and receives a stent, after having been created.

The method 500 uses a channel creating apparatus, such as, for example, an embodiment of the apparatus described hereinabove such as electrosurgical device 100, defining an apparatus distal end portion, such as for example the distal tip 108 described hereinabove, insertable into the body vessel 600. The channel creating apparatus, such as electrosurgical device 100 includes an energy delivery component, such as electrode tip 112 operatively coupled to the apparatus distal end portion for delivering energy proximate the apparatus distal end portion.

The method 500 starts at step 505. Then, at step 510, the apparatus distal end portion is inserted into the body vessel 604.

Afterwards, at step 515, the apparatus distal end portion is positioned proximate the occlusion harder portion 606 and, at step 520, a channel first portion 610 of the channel 600 is created through the occlusion harder section 606. This channel first portion may also be referred to as a channel harder portion. Creating the channel first portion 610 includes delivering the energy into the occlusion harder portion 606.

Subsequently, at step 525, the apparatus distal end portion is positioned proximate the occlusion softer portion 608 and, at step 530, a channel second portion 612 of the channel 600 is created through the occlusion softer portion 608 by pushing the apparatus distal end portion through at least a portion of the occlusion softer portion 608, the channel second portion 612 being created substantially without using the energy delivery component such as electrode tip 112, to deliver energy into the occlusion softer portion 608. This channel second portion may be referred to as a channel softer portion. At this point one or more of the steps within the method may be repeated in order to complete the procedure, for example to traverse through the occlusion. In some examples, the method is ended at step 535, for example once the occlusion has been traversed.

For example, the apparatus distal end portion is pushed by applying a substantially longitudinal force to an apparatus proximal portion (for example, the proximal region of the apparatus described hereinabove) longitudinally opposed to the apparatus distal end portion. In another example, the apparatus distal end portion is pushed directly, for example using a motor or any other actuator coupled to the apparatus distal end portion.

It should be noted that while embodiments of the apparatus described hereinabove are usable to perform the method 500, in other embodiments of the invention, any suitable apparatus may be used.

Also, while in the method 500 the channel first portion 610 is created before the channel second portion 612, it is within the scope of the invention to create the channel second portion 612 before the channel first portion 610.

It has been found that the method embodied in FIGS. 5 and 6 leads to a new and unexpected result in which the channel 600 is created relatively easily and relatively safely through both the occlusion harder and softer portions 606 and 608 using the same apparatus, such as electrosurgical device 100. In addition, channel 600 may be created by an apparatus whose mechanical properties are substantially similar to those of standard mechanical guide-wires. Other advantages of the proposed methods have been mentioned hereinabove.

In some embodiments of the invention, the occlusion harder portion 606 has a hardness that is substantially too large to allow pushing the apparatus distal end portion through the occlusion harder portion 606 without delivering the energy into the occlusion harder portion 606. For example, it was found that when the occlusion harder portions 606 has a hardness such that a mechanical pressure of at least about 20 kg/cm2 is required to create a channel thereinto, conventional mechanical guide-wires are typically unusable to create the channel first portion 610. These embodiments of the present invention thus provide a means for traversing an occlusion that standard mechanical guide-wires may be unable to penetrate.

In some embodiments of the invention, step 520 is performed as follows. First, a channel first portion first segment 614 is created through the occlusion harder portion 606 while delivering the energy into the occlusion harder portion 606 and the apparatus distal end portion is advanced through the channel first portion first segment 614. The advancement of the apparatus distal end portion may be simultaneous with or subsequent to the delivery of energy. When the channel first portion first segment 614 has been created, the delivery of energy is stopped. Afterwards, a user of the channel creating apparatus may attempt to push the apparatus distal end portion through the occlusion 602 substantially without delivering energy via the energy delivery component such as electrode tip 112. Upon the apparatus distal end portion being unable to be pushed through the occlusion 602 after having created the channel first portion first segment 614, a channel first portion second segment 616 extending from the channel first portion first segment 614 is created similarly to the channel first portion first segment 614. If required, additional segments of the channel first portion 610 are also similarly created. If the apparatus distal end portion can be pushed through the occlusion 602, the creation of the channel 600 continues as described with respect to the creation of the channel second portion 612.

Therefore, by repeatedly testing for the possibility of creating the channel mechanically after, for example, each energy delivery step, an intended user may lower the risk that the energy delivered may injure tissues that should remain intact, such as for example the vessel wall 618 of the body vessel 604.

In some embodiments of the invention, the energy is delivered for a predetermined amount of time before stopping the delivery of the energy. In other embodiments, the user may decide, during the course of the procedure, on the amount of time during which energy should be delivered. For example, the amount of time during which energy may be delivered may be from about 0.1 seconds to about 5 seconds. In a more specific embodiment of the invention, the amount of time during which energy is delivered for a duration of from about 0.5 second to about 3 seconds. It has been found that these amounts of time allow for the creation of the channel 600 in a reasonable amount of time while reducing the risk of unwanted injuries. During the periods of time described above, the energy may be delivered continuously or as a pulsed waveform.

In other embodiments of the invention, when performing step 520, the intended user assesses continuously, periodically or intermittently the position of the apparatus distal end portion relatively to the occlusion softer portion 608. Upon detection that the apparatus distal end portion is located proximate the occlusion softer portion 608, the delivery of the energy is stopped and the channel second portion 612 is created. For example, the position of the apparatus distal end portion is assessed using a position assessment method selected from the group consisting of an imaging technique, an impedance measurement, a measurement of a force exerted onto the apparatus distal end portion, a measurement of a pressure exerted onto the apparatus distal end portion and a measurement based on ultrasonic signals, among other possibilities.

In these embodiments, assessing the position of the apparatus distal end portion may allow the user to deliver energy to the occlusion 602 over a minimal duration, which again may lower the risk of injuring structures adjacent to the occlusion 602.

In some embodiments, if a user is unable to mechanically advance the apparatus through the occlusion softer portion, the user may choose to deliver energy via the energy delivery component, such as electrode tip 112, or may attempt to re-orient at least a portion of the apparatus. As described hereinabove, such re-orientation may take the form of steering the device in some manner or, alternatively, applying torque to a portion of the device. In some such embodiments, the position of the apparatus may be assessed, as described hereinabove, prior to choosing which course of action to follow.

In some particular situations, an occlusion may comprise another, relatively hard, portion, for example on the opposite end of the first hard portion. In such embodiments, a channel third portion may be created through this hard portion of the occlusion in substantially the same manner as the channel first portion, described hereinabove.

As mentioned hereinabove, the energy delivered may be any suitable energy. For example, the energy may be radio-frequency electromagnetic energy or radiant energy, for example laser light, among other possibilities. When radio-frequency energy is used, it has been found that radio-frequency energy delivered with a power of at least about 5 W at a voltage of at least about 75 Volts (peak-to-peak) produces good channel creation performances while remaining relatively safe for the patient. Also, the use of radio-frequency energy is advantageous as it allows the use of relatively small apparatus distal end portions that are relatively robust, and which therefore are relatively well suited to the creation of the channel second portion 612 using mechanical forces.

In such embodiments, when the distal end portion is re-oriented during the creation of channel 600, energy may be delivered via the energy delivery component, such as electrode tip 112, even in the occlusion softer portion 608, in order to facilitate the re-orientation of the distal end portion.

In some embodiments of the invention, the energy delivery component, such as electrode tip 112 is selectively operable in an energy delivering state and a deactivated state. In the energy delivering state, the energy is delivered proximate the apparatus distal end portion. In the deactivated state, the energy is substantially not delivered proximate the apparatus distal end portion.

When such an energy delivery component, such as electrode tip 112 is used, the method 500 may be performed such that the channel first portion 610 is created through the occlusion harder section 606 by operating the energy delivery component, such as electrode tip 112 in the energy delivering state and delivering the energy into the occlusion harder portion 606. The channel second portion 612 is created through the occlusion softer portion 608 by operating the energy delivery component, such as electrode tip 112 in the deactivated state and pushing the apparatus distal end portion through at least a portion of the occlusion softer portion 608.

An advantageous, but non-limiting, embodiment of the invention using such an energy delivery component, such as electrode tip 112 is one wherein the channel creating apparatus includes a pressure sensor operatively coupled to the apparatus distal end portion for measuring a pressure exerted onto the occlusion by the apparatus distal end portion. Then, in some embodiments of the invention, the method 500 includes operating the energy delivery component, such as electrode tip 112 in the energy delivering state if the measured pressure is substantially above a predetermined pressure and operating the energy delivery component, such as electrode tip 112 in the deactivated state if the measured pressure is substantially below the predetermined pressure. The predetermined pressure is, for example, the pressure at which mechanical penetration is difficult or impossible. The energy delivery is manually switched on or off, or the channel creating apparatus includes a controller for automatically turning the energy delivering apparatus to the deactivated state if the pressure exerted onto the occlusion by the apparatus distal end portion is substantially below the predetermined pressure and turning the energy delivery apparatus to the energy delivering state if the pressure exerted onto the occlusion by the apparatus distal end portion is substantially above a predetermined pressure.

In these embodiments, the activation of energy delivery occurs only if the energy is required to create the channel 600 or a portion thereof. Otherwise, only a mechanical force is used to create the channel 600. This reduces uncertainty and variability in the manner in which the method is performed. Also, by reducing or eliminating the need to repeatedly test for the possibility of creating the channel mechanically, the method may be performed relatively fast with relatively low risks of injuring the patient.

In some embodiments of the invention, if an intended user is unable to push the apparatus distal end portion through the occlusion softer portion 608, the intended user may reorient the apparatus distal end portion within the occlusion softer portion 608 and attempt to push the apparatus distal end portion through the occlusion softer portion 608 substantially without delivering energy via the energy delivery component, such as electrode tip 112. However, in some embodiments of the invention, energy is used to facilitate the reorientation of the apparatus distal end portion.

In any or all of the embodiments described herein, a user may elect to initially use a standard mechanical guide-wire to attempt to penetrate an occlusion. Once a hard portion of the occlusion is encountered, the method 500 as described hereinabove may be employed.

In some embodiments of the invention, the energy delivery apparatus such as electrosurgical device 100 is used such that a channel 600 is created at least partially through the occlusion. This channel may be created by delivering energy through the electrode tip 112 and advancing the apparatus distal end portion such as distal tip 108 into the occlusion 602 simultaneously or after delivering energy.

In some embodiments of the invention, when the intended user of the energy delivery apparatus such as electrosurgical device 100 finds that advancing through the occlusion 602 or any other material becomes relatively difficult, the intended user may retract the apparatus distal end portion and apply electrical energy while a gap exists between the apparatus distal end and the target location. Then, a channel 600 may be created more easily, for example due to the space created between the electrode tip 112 and the occlusion 602. Afterwards, the apparatus distal end portion may then be further advanced through this channel.

In some embodiments of the present invention, as mentioned previously, energy may be delivered from the electrode tip 112 in either a continuous mode or a discontinuous mode. In one example, a continuous mode is used and power is supplied to sustain arcing for a period of about 3 seconds in order to facilitate traversal through an occlusion harder portion 606. In an alternate example, a discontinuous mode is used and power is supplied for a period of about 10 seconds. In one example, power is supplied at a frequency of 1 Hz.

In one embodiment of the method of the present invention, the energy delivery device such as the electrosurgical device 100 is advanced to a target location such as within an elongated vessel 604 within a patient's body. The energy delivery portion such as electrode tip 112 is positioned adjacent an occlusion 602. As outlined above, energy is delivered through the energy delivery portion, such as electrode tip 112, to initiate arcing allowing device 100 to form a portion of the channel 600 through the occlusion, such as through an occlusion harder portion 606. The electrode tip 112 and the electrosurgical device 100 are mechanically advanced through the occlusion softer portion 608, creating another portion of channel 600. In one embodiment, the electrosurgical device 100 is substantially rigid/stiff along a portion thereof. After a substantial segment of the occlusion 602 has been crossed. A dilation catheter may be advanced over the electrosurgical device 100, in order to further enhance/widen the channel 600. The electrosurgical device 100 is sufficiently stiff along a portion thereof to allow it to function as a rail allowing the dilation catheter to be advanced over it. The dilation catheter having a wider outer diameter along at least a portion thereof, allows the channel 600 within the occlusion 604 to be widened. The dilation catheter may then be withdrawn and a balloon catheter may then be advanced over the electrosurgical device and positioned within the channel 600 created by electrosurgical device 100. The balloon may then be inflated to further dilate or widen the channel 600. The dilation using a balloon catheter may be performed once or multiple times in order to dilate the channel 600.

In an alternate embodiment, the electrosurgical device 100 defines a device distal region 104 having a distal end portion, such as distal tip 108, that has an outer diameter (OD) that is wider than the OD of a proximal portion of the device distal region 104. In one example, the distal end portion of the electrosurgical device has an outer diameter of thou (i.e. 5 thousandths of an inch) at the distal tip 108. The outer diameter of the device distal region 104 then tapers proximally to 25 thou. As mentioned previously, in one example, a proximal portion of the device proximal region 106 has an outer diameter that is wider than the distal tip 108 of the electrosurgical device 100. As the electrosurgical device 100 is 10 advanced through the occlusion 602 the proximal portion of the device proximal region 106 functions to dilate the channel 600. This may help to minimize the step of inserting a dilating catheter over the electrosurgical device 100 in order to further dilate the occlusion. The electrosurgical device 100 thus functions both to traverse through the occlusion (both occlusion harder portions 606 and occlusion softer portions 608) by forming a channel 600 and additionally may function to dilate the channel 600 as it is formed. Thus the step of inserting a dilating catheter may be minimized. A balloon catheter may then be advanced directly over the electrosurgical device 100 and one or more inflations may be used to further wider the channel 600.

In one broad aspect, embodiments of the present invention provide an electrosurgical device for creating a channel through a region of tissue using energy provided by an electrical energy source, the electrosurgical device comprising: a core wire for receiving the energy from the electrical energy source; an electrode tip provided at a distal end of the core wire for delivery of the energy to the region of tissue, the electrode tip being electrically coupled to the core wire; an electrical insulation surrounding the core wire, the electrical insulation comprising at least one inner insulation layer and at least one outer insulation layer; a hydrophilic coating applied to an outer most insulation layer of the at least one outer insulation layer; and an electrically insulative thermal shield disposed between a proximal end of the electrode tip and the electrical insulation for thermally protecting the electrical insulation from heat produced by the delivery of the energy through the electrode tip.

In another broad aspect, the present inventors have discovered a hydrophilic RF guidewire that is capable of delivering RF for creating a channel through a region of tissue where the RF guidewire comprises a hydrophilic coating along a portion thereof to reduce friction and for ease of traversal and/or navigation through vasculature and/or tissue: (i) sufficient electrical resistivity to minimize the risk of leakage current to maintain patient safety upon delivery of RF and (i) sufficient mechanical flexibility to enable navigation through vascular anatomy to allow the RF guidewire to reach the intended target. In some such embodiments, a hydrophilic RF guidewire is provided that overcomes the limitations associated with prior art guidewires while maintaining its mechanical and electrical properties.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A wire for navigating tortuous vasculature and creating a channel through a region of tissue using energy provided by an electrical energy source, the wire comprising:
    a core wire for receiving the energy from the electrical energy source;
    an electrode tip provided at a distal end of the core wire for delivery of the energy to the region of tissue, the electrode tip being electrically coupled to the core wire;
    an electrical insulation surrounding the core wire, the electrical insulation comprising at least one inner insulation layer and at least one outer insulation layer;
    a hydrophilic coating applied to an outer most insulation layer of the at least one outer insulation layer;
    a thermal shield which is electrically insulative disposed between a proximal end of the electrode tip and the electrical insulation for thermally protecting the electrical insulation from heat produced by the delivery of the energy through the electrode tip; and
    the thermal shield having a first outer diameter which is constant along a distal portion of the thermal shield and a second outer diameter which is constant along a proximal portion of the thermal shield wherein the first outer diameter is greater than the second outer diameter, wherein the electrical insulation is formed around the proximal portion of the thermal shield providing a smooth transition of an outer surface between the distal portion of the thermal shield and the electrical insulation whereby an outer diameter of the wire is constant along the distal portion of the thermal shield and the proximal portion of the thermal shield.

2. The wire of claim 1, further comprising a support structure for supporting the electrode tip, the support structure having a proximal end, wherein the proximal end of the support structure is positioned distally with respect to a distal end of the thermal shield.

3. The wire of claim 1, wherein the at least one inner insulation layer comprises one or more inner polymer layers and wherein the at least one outer insulation layer comprises one or more outer polymer layers.

4. The wire of claim 3, wherein the at least one inner insulation layer comprises an electrically resistive inner insulation layer in contact with the core wire along a length of the core wire.

5. The wire of claim 4, wherein the electrically resistive inner insulation layer comprises a polymer defining an electrically resistive inner polymer layer.

6. The wire of claim 5, wherein the electrically resistive inner polymer layer has a di-electric constant that is greater than the di-electric constant of the one or more outer polymer layers.

7. The wire of claim 5, wherein the electrically resistive inner polymer layer has a width that is less than the width of the at least one outer insulation layer.

8. The wire of claim 5, wherein the electrical insulation comprises:
    a proximal insulation segment, the proximal insulation segment comprising the electrically resistive inner polymer layer and a substantially rigid outer polymer layer that surrounds the electrically resistive inner polymer layer, the proximal insulation segment being substantially rigid for allowing for pushability and torquability;
an intermediate insulation segment, wherein the intermediate insulation segment comprises the electrically resistive inner polymer layer, a substantially rigid outer polymer layer surrounding the electrically resistive inner polymer layer partially along a radial width of the electrosurgical device, a substantially flexible outer polymer layer surrounding the electrically resistive inner polymer layer partially along a radial width of the electrosurgical device, the intermediate insulation segment being more flexible than the proximal insulation segment to allow the electrosurgical device to be advanced through tortuous vasculature; and
a distal insulation segment comprising a thermal barrier for protecting the intermediate and proximal insulation segments from the delivery of energy from the electrode tip and the heat produced thereby;
wherein the hydrophilic coating is disposed along the substantially rigid outer polymer layer along the proximal insulation segment and the substantially flexible outer polymer layer along the intermediate insulation segment wherein the substantially rigid outer polymer layer along the proximal insulation segment and the substantially flexible outer polymer layer along the intermediate insulation segment, enable the hydrophilic coating to be disposed thereon.

9. The wire of claim 8, wherein the hydrophilic coating is selected from the group consisting of: hyaluronic acid (HA), and a hydrogel.

10. The wire of claim 9, wherein the hydrogel selected from the group consisting of: polyvinylpyrrolidone (PVP), poly (ethylene oxide) (PEO) or poly (ethylene glycol) (PEG).

11. The wire of claim 8, wherein the thermal shield comprises a ceramic thermal shield.

12. The wire of claim 11, wherein the ceramic thermal shield is tubular.

13. The wire of claim 8, wherein an area where the distal and intermediate insulation segments meet forms a joint where the substantially flexible outer polymer layer of the intermediate insulation segment overlaps and is positioned over the thermal barrier of the distal insulation segment.

14. The wire of claim 8, wherein an area where the distal and intermediate insulation segments meet forms a joint where the thermal barrier of the distal insulation segment overlaps and is positioned over the substantially flexible outer polymer layer of the intermediate insulation segment.

15. The wire of claim 1, wherein the outer most insulation layer comprises a non-fluorinated polymer.

16. The wire of claim 15, wherein the outer most insulation layer is selected from the group consisting of: polyimide, polyamide-imide, and polyether ether ketone (PEEK), polyurethane, nylon, polypropylene, silicone, polyether block amide, and high density polyethylene (HDPE).

17. The wire of claim 1, wherein the at least one inner insulation layer and the at least one outer insulation layer, other than the outer most insulation layer, are selected from the group consisting of: polyimide, polyamide-imide, and polyether ether ketone (PEEK), polytetrafluoroethylene (PTFE), Polyethylene terephthalate (PET) polyurethane, nylon, polypropylene, silicone, polyether block amide, and High Density Polyethylene (HDPE).

18. The wire of claim 1 wherein the thermal shield comprises a discrete change in outer diameter between the first outer diameter and second outer diameter.

* * * * *